(12) United States Patent
Jamshidi et al.

(10) Patent No.: US 12,011,719 B2
(45) Date of Patent: Jun. 18, 2024

(54) DIGITAL MICROFLUIDIC SYSTEM FOR SINGLE-CELL ISOLATION AND CHARACTERIZATION OF ANALYTES

(71) Applicant: Illumina, Inc., San Diego, CA (US)

(72) Inventors: Arash Jamshidi, San Francisco, CA (US); Yan-you Lin, San Francisco, CA (US); Farnaz Absalan, San Francisco, CA (US); Sarah Stuart, San Francisco, CA (US); Gordon Cann, San Francisco, CA (US); Yir-Shyuan Wu, San Francisco, CA (US); Tarun Khurana, San Francisco, CA (US); Jeffrey S Fisher, San Francisco, CA (US)

(73) Assignee: Illumina, Inc., San Diego, CA (US)

( * ) Notice: Subject to any disclaimer, the term of this patent is extended or adjusted under 35 U.S.C. 154(b) by 26 days.

(21) Appl. No.: 17/555,013

(22) Filed: Dec. 17, 2021

(65) Prior Publication Data

US 2022/0184622 A1 Jun. 16, 2022

Related U.S. Application Data

(62) Division of application No. 15/779,459, filed as application No. PCT/US2016/064206 on Nov. 30, 2016, now Pat. No. 11,203,016.

(60) Provisional application No. 62/358,968, filed on Jul. 6, 2016, provisional application No. 62/314,071, filed on Mar. 28, 2016, provisional application No. 62/281,510, filed on Jan. 21, 2016, provisional application No. 62/261,786, filed on Dec. 1, 2015.

(51) Int. Cl.
| | |
|---|---|
| *B01L 3/00* | (2006.01) |
| *C12Q 1/6806* | (2018.01) |
| *G01N 1/28* | (2006.01) |
| *G01N 33/543* | (2006.01) |
| *C12Q 1/6869* | (2018.01) |
| *G01N 15/10* | (2006.01) |

(52) U.S. Cl.
CPC ... *B01L 3/502761* (2013.01); *B01L 3/502784* (2013.01); *B01L 3/5088* (2013.01); *C12Q 1/6806* (2013.01); *G01N 1/28* (2013.01); *G01N 33/54333* (2013.01); *B01L 2200/0605* (2013.01); *B01L 2200/0642* (2013.01); *B01L 2200/0668* (2013.01); *B01L 2300/0819* (2013.01); *B01L 2300/165* (2013.01); *B01L 2400/0427* (2013.01); *B01L 2400/043* (2013.01); *C12Q 1/6869* (2013.01); *C12Q 2563/143* (2013.01); *C12Q 2563/149* (2013.01); *C12Q 2563/185* (2013.01); *G01N 2015/1006* (2013.01)

(58) Field of Classification Search
CPC ......... B01L 3/502761; B01L 3/502784; B01L 2200/0668; C12Q 1/6806
See application file for complete search history.

(56) References Cited

U.S. PATENT DOCUMENTS

| | | | |
|---|---|---|---|
| 2007/0243523 A1 | 10/2007 | Ionescu-Zanetti et al. | |
| 2008/0044893 A1* | 2/2008 | Pollack | C30B 29/58 |
| | | | 422/63 |
| 2009/0311713 A1* | 12/2009 | Pollack | B01L 7/525 |
| | | | 435/287.2 |
| 2012/0148140 A1* | 6/2012 | Di Carlo | G01N 1/31 |
| | | | 382/133 |
| 2013/0302883 A1* | 11/2013 | Fowler | C12P 19/34 |
| | | | 435/287.2 |
| 2014/0248621 A1 | 9/2014 | Collins | |
| 2014/0262787 A1 | 9/2014 | Molho et al. | |
| 2015/0072900 A1 | 3/2015 | Srinivasan et al. | |
| 2015/0141261 A1 | 5/2015 | Hunicke-Smith et al. | |
| 2015/0204862 A1* | 7/2015 | Fan | G01N 33/54366 |
| | | | 506/9 |
| 2015/0253284 A1 | 9/2015 | Sudarsan et al. | |

FOREIGN PATENT DOCUMENTS

| | | |
|---|---|---|
| JP | 2015519911 A | 7/2015 |
| KR | 10-2015-0048541 A | 7/2015 |
| WO | 2015009967 A1 | 1/2015 |

(Continued)

OTHER PUBLICATIONS

Di Carlo, Dino, "Dynamic single cell culture array", Lab on a chip: Miniaturisation for chemistry, physics, biology, materials science and bioengineering, vol. 6, No. 11, Jan. 1, 2006, 1445.

(Continued)

*Primary Examiner* — Sahana S Kaup
(74) *Attorney, Agent, or Firm* — Gavrilovich, Dodd & Lindsey LLP

(57) ABSTRACT

In accordance with embodiments herein a method for capturing cells of interest in a digital microfluidic system is provided, comprising utilizing a droplet actuator to transport a sample droplet to a microwell device. The microwell device includes a substrate having a plurality of microwells that open onto a droplet operations surface of the microwell device. The sample droplet includes cells of interest that enter the microwells. The method introduces capture beads to the microwells, and the capture elements are immobilized on the capture beads. The method utilizes the droplet actuator to transport a cell lysis reagent droplet to the microwell device. Portions of the cell lysis reagent droplet enter the microwells and, during an incubation period, cause the cells of interest to release analyte that is captured by the capture elements on the capture beads.

9 Claims, 22 Drawing Sheets

(56) References Cited

FOREIGN PATENT DOCUMENTS

| WO | 2015/031849 A1 | 3/2015 | |
|---|---|---|---|
| WO | 2016040476 A1 | 3/2016 | |
| WO | WO-2016040476 A1 * | 3/2016 | ......... C12N 15/1096 |

OTHER PUBLICATIONS

Nilsson et al., "Review of cell and particle trapping in microfluidic systems", Analytica Chimica Acta, vol. 649, No. 2, 141-157, Sep. 7, 2009.
Rettig et al, "Large-scale single-cell trapping and imaging using microwell arrays", Analytical Chemistry, American Chemical Society, vol. 77, No. 17, Sep. 1, 2005, pp. 5628-5634.
Rissin et al., "Single-molecule enzyme-linked immunosorbent assay detects serum proteins at subfemtomolar concentrations", Nature Biotechnology, vol. 28, No. 6, Jun. 1, 2010, pp. 595-599.
Thompson et al., "Microfluidics for single-cell genetic analysis", Lab on a Chip: Miniaturisation for Chemistry, Physics, Biology, Materials Science and Bioengineering, vol. 14, No. 17, Mar. 31, 2014, p. 3135.
Yamamura et al., "Single-cell microarray for analyzing cellular response", Analytical Chemistry, American Chemical Society, vol. 77, No. 24, Nov. 12, 2005, pp. 8050-8056.
Van Lith, Joris, International Search Report and Written Opinion, PCT/US2016/064206, International Searching Authority, European Patent Office, dated Feb. 20, 2017, 14 pages.
Van Lith, Joris, Office Action, Application No. 16816512.4, European Patent Office, dated Mar. 18, 2020.
European Patent Office, EP21170333.5, Office Action, dated Oct. 7, 2021.
Matsuoka, Tomoya, Office Action, Application No. 2018-527217, Japan Patent Office, dated Jul. 2, 2019.

* cited by examiner

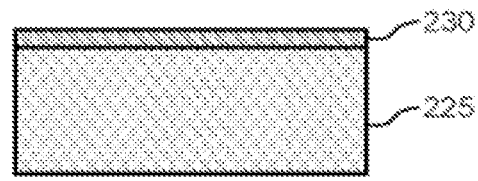
Figure 3A
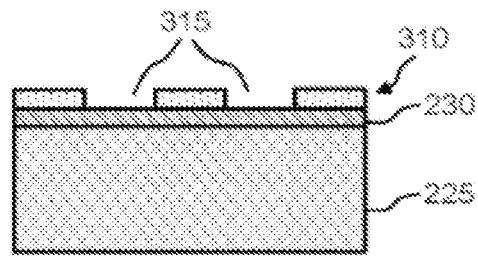
Figure 3B
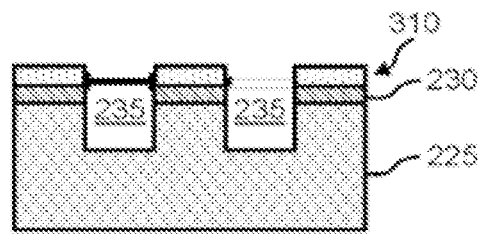
Figure 3C
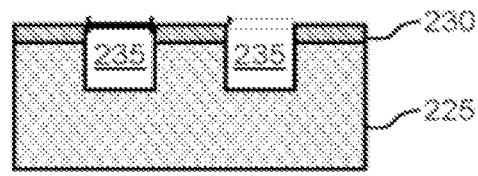
Figure 3D

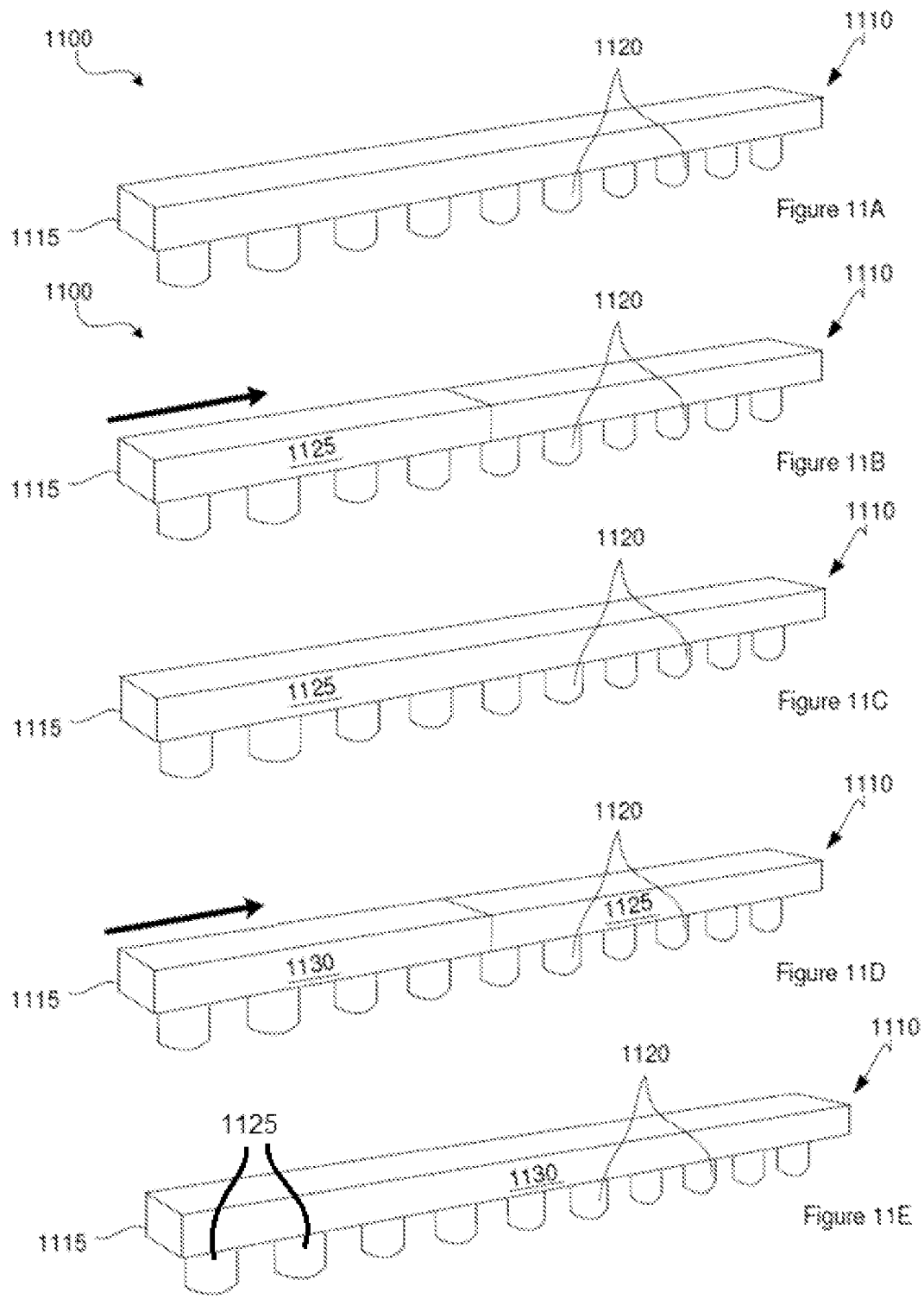

ns and Methods for
DIGITAL MICROFLUIDIC SYSTEM FOR SINGLE-CELL ISOLATION AND CHARACTERIZATION OF ANALYTES

CROSS-REFERENCE TO RELATED APPLICATIONS

The present application is a divisional of U.S. patent application Ser. No. 15/779,459, filed May 25, 2018, which application is a U.S. National Stage Application filed under 35 U.S.C. § 371 and claims priority to PCT/US2016/064206, filed Nov. 30, 2016, which application claims priority to U.S. Provisional Application No. 62/314,071, filed Mar. 28, 2016; U.S. Provisional Application No. 62/281,510, filed Jan. 21, 2016; U.S. Provisional Application No. 62/261,786, filed Dec. 1, 2015; and U.S. Provisional Application No. 62/358,968, filed Jul. 6, 2016. The complete subject matter of all of the above applications is hereby expressly incorporated by reference in their entirety.

BACKGROUND OF THE INVENTION

The importance of single-cell level data (e.g., next-generation sequencing data) is increasingly appreciated in a wide variety of medical and research areas. Accordingly, a number of technologies have been developed for the analysis of single cells. Common to many of these technologies is the need to physically segregate individual cells and maintain cell-of-origin information in subsequent processing and analysis steps. In one example, channel-based droplet fluidics has been used for automated isolation and barcoding of multiple single cells in a sample for sequencing. However, some downstream process steps in construction of a sequencing library may not be automated and a manual workflow is required. There is a need for a flexible, automated platform for single-cell isolation and subsequent characterization of analytes (e.g., preparation of sequencing-ready single-cell libraries).

Definitions

As used herein, the following terms have the meanings indicated.

"Activate," with reference to one or more electrodes, means affecting a change in the electrical state of the one or more electrodes which, in the presence of a droplet, results in a droplet operation. Activation of an electrode can be accomplished using alternating current (AC) or direct current (DC). Any suitable voltage may be used which effects the desired operation, such as a droplet operation. For example, an electrode may be activated using a voltage which is greater than about 150 V, or greater than about 200 V, or greater than about 250 V, or from about 275 V to about 1000 V, or about 300 V. Where an AC signal is used, any suitable frequency may be employed which effects the desired operation, such as a droplet operation. For example, an electrode may be activated using an AC signal having a frequency from about 1 Hz to about 10 MHz, or from about 10 Hz to about 60 Hz, or from about 20 Hz to about 40 Hz, or about 30 Hz.

"Bead," with respect to beads on a droplet actuator, means any bead or particle that is capable of interacting with a droplet on or in proximity with a droplet actuator.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; non-limiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For non-limiting examples of droplet fluids that may be subjected to droplet operations using the approach of the present disclosure, see Eckhardt et al., International Patent Pub. No. WO/2007/120241, entitled, "Droplet-Based Biochemistry," published on Oct. 25, 2007, the entire disclosure of which is incorporated herein by reference. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. A droplet can include nucleic acids, such as DNA, genomic DNA, RNA, mRNA or analogs thereof; nucleotides such as deoxyribonucleotides, ribonucleotides, or analogs thereof such as analogs having terminator moieties such as those described in Bentley et al., Nature 456:53-59 (2008); Gormley et al., International Patent Pub. No. WO/2013/131962, entitled, "Improved Methods of Nucleic Acid Sequencing," published on Sep. 12, 2013; Barnes et al., U.S. Pat. No. 7,057,026, entitled "Labelled Nucleotides," issued on Jun. 6, 2006; Kozlov et al., International Patent Pub. No. WO/2008/042067, entitled, "Compositions and Methods for Nucleotide Sequencing," published on Apr. 10, 2008; Rigatti et al., International Patent Pub. No. WO/2013/117595, entitled, "Targeted Enrichment and Amplification of Nucleic Acids on a Support," published on Aug. 15, 2013; Hardin et al., U.S. Pat. No. 7,329,492, entitled "Methods for Real-Time Single Molecule Sequence Determination," issued on Feb. 12, 2008; Hardin et al., U.S. Pat. No. 7,211,414, entitled "Enzymatic Nucleic Acid Synthesis: Compositions and Methods for Altering Monomer Incorporation Fidelity," issued on May 1, 2007; Turner et al., U.S. Pat. No. 7,315,019, entitled "Arrays of Optical Confinements and Uses Thereof," issued on Jan. 1, 2008; Xu et al., U.S. Pat. No. 7,405,281, entitled "Fluorescent Nucleotide Analogs and Uses Therefor," issued on Jul. 29, 2008; and Rank et al., U.S. Patent Pub. No. 20080108082, entitled "Polymerase Enzymes and Reagents for Enhanced Nucleic Acid Sequencing," published on May 8, 2008, the entire disclosures of which are incorporated herein by reference; enzymes such as polymerases, ligases, recombinases, or transposases; binding partners such as antibodies, epitopes, streptavidin, avidin, biotin, lectins or carbohydrates; or other biochemically active molecules. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include one or more beads.

"Droplet Actuator" means a device for manipulating droplets. For examples of various structural components of droplet actuators suitable for use in the present invention, see Pamula et al., U.S. Pat. No. 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Microfluidics and Methods for Using Same," issued on Aug. 10, 2004; Shenderov, U.S. Pat. No. 6,565,727, entitled "Actuators for Microfluidics Without Moving Parts," issued on May 20, 2003; Kim et al., U.S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, U.S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010), the entire disclosures of which are incorporated herein by reference. Certain droplet actuators will include one or more substrates arranged with a droplet operations gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the present disclosure. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™. Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define on-actuator dispensing reservoirs. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of techniques for controlling droplet operations that may be used in the droplet actuators of the present disclosure include using devices that induce hydrodynamic fluidic pressure, such as those that operate on the basis of mechanical principles (e.g., external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g., gas bubble generation/phase-change-induced volume expansion); other kinds of surface-wetting principles (e.g., electrowetting, and opto-electrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the present disclosure. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap). Droplet operations surfaces of certain droplet actuators of the present disclosure may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. In some cases, the droplet operations surface may include a hydrophobic coating. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT:PSS). Other examples of electrically conducting organic polymers and alternative conductive layers are described in Pollack et al., International Patent Pub. No. WO/2011/002957, entitled "Droplet Actuator Devices and Methods," published on Jan. 6, 2011, the entire disclosure of which is incorporated herein by reference. One or both substrates may be fabricated using, for example, a printed circuit board (PCB), glass, indium tin oxide (ITO)-coated glass, and/or semiconductor materials as the substrate.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (e.g., the volume of the resulting droplets can be the same or different) or number of resulting droplets (the number of resulting droplets may be 2, 3, 4, 5, or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical features, such as obstacles, gap height changes, or surface indentations. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., U.S. Patent Pub. No. 20100194408, entitled "Capacitance Detection in a Droplet Actuator," published on Aug. 5, 2010, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is sometimes helpful (though not an absolute requirement) for conducting droplet operations for the footprint area of droplet to be similar to electrowetting area; in other words, 1×-, 2×- 3×-droplets are usefully controlled operated using 1, 2, and 3 electrodes, respectively. If the droplet footprint is greater than number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be or include a low-viscosity oil, such as silicone oil or hexadecane filler fluid. The filler fluid may be or include a halogenated oil, such as a fluorinated or perfluorinated oil. The filler fluid may fill the entire gap of the droplet actuator or may coat one or more surfaces of the droplet actuator. Filler fluids may be conductive or non-conductive. Filler fluids may be selected to improve droplet operations and/or reduce loss of reagent or target substances from droplets, improve formation of microdroplets, reduce cross contamination between droplets, reduce contamination of droplet actuator surfaces, reduce degradation of droplet actuator materials, etc. Examples of filler fluids and filler fluid formulations suitable for use with the methods and apparatus set forth herein are provided in Srinivasan et al, International Patent Pub. No. WO/2010/027894, entitled "Droplet Actuators, Modified Fluids and Methods," published on Jun. 3, 2010; Srinivasan et al, International Patent Pub. No. WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Jan. 15, 2009; and Monroe et al., U.S. Patent Pub. No. 20080283414, entitled "Electrowetting Devices," published on Nov. 20, 2008, the entire disclosures of which are incorporated herein by reference, as well as the other patents and patent applications cited herein. Fluorinated oils may in some cases be doped with fluorinated surfactants, e.g., Zonyl FSO-100 (Sigma-Aldrich) and/or others. A filler fluid is typically a liquid. In some embodiments, a filler gas can be used instead of a liquid.

"Reservoir" means an enclosure or partial enclosure configured for holding, storing, and/or supplying liquid. A droplet actuator system of the present disclosure may include on-cartridge reservoirs and/or off-cartridge reservoirs. On-cartridge reservoirs may, for example, include (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a film between such liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

The terms "fluidics cartridge," "digital fluidics cartridge," "droplet actuator," and "droplet actuator cartridge" as used throughout the description can be synonymous.

BRIEF DESCRIPTION OF THE INVENTION

In accordance with embodiments herein a method for capturing cells of interest in a digital microfluidic system is provided, comprising utilizing a droplet actuator to transport a sample droplet to a microwell device. The microwell device includes a substrate having a plurality of microwells that open onto a droplet operations surface of the microwell device. The sample droplet includes cells of interest that enter the microwells. The method introduces capture beads to the microwells, and the capture elements are immobilized on the capture beads. The method utilizes the droplet actuator to transport a cell lysis reagent droplet to the microwell device. Portions of the cell lysis reagent droplet enter the microwells and, during an incubation period, cause the cells of interest to release analyte that is captured by the capture elements on the capture beads.

Optionally, the method may further comprise utilizing the droplet actuator to transport the sample droplet away from the microwell device while leaving at least a portion of the cells of interest captured in the microwells. The method may permit at least a portion of the cells of interest to settle into the microwells. The droplet operations surface of the microwell device may include interstitial areas between microwells that are hydrophobic such that substantially no residue of the cells of interest or capture beads remains on the droplet operations surface of the microwell device. The method may remove the capture beads with the analyte captured thereon from the microwells. The removing operation may include positioning a magnet proximate to the microwells to form a magnetic field that pulls the capture beads from the microwells. The method may utilize a magnetic field to move the capture beads to and away from the microwells.

Optionally, each of the capture beads may include a plurality of the capture elements. The plurality of capture elements may include a capture sequence and a unique barcode sequence. The capture sequence may be one of i) a poly-T sequence for capture of total mRNA, or ii) a plurality of transcript-specific capture sequences that target a panel of genes of interest. The capture beads may be sized such that only one of the capture beads fits in one of the microwells. The capture beads may be deposited in the microwells by gravity. The capture beads may be magnetic and are deposited in the microwells utilizing a magnetic attraction.

In accordance with embodiments herein a digital fluidics system for capturing cells of interest is provided, comprising a droplet actuator that includes a droplet operations gap. The droplet actuator includes droplet operations electrodes arranged proximate to the droplet operations gap. A microwell device includes a substrate. The microwell device includes microwells formed in the substrate. The microwells open onto a droplet operations surface of the microwell device. The microwell device is coupled to the droplet actuator and positioned such that the microwells face the droplet operations gap. The controller is configured to execute program instructions to direct the droplet actuator to transport a sample droplet to a microwell device. The sample droplet includes cells of interest that enter the microwells.

The controller further introduces capture beads to the microwells, wherein capture elements are immobilized on the capture beads and directs the droplet actuator to transport a cell lysis reagent droplet to the microwell device. Portions of the lysis reagent droplet enter the microwells and, during an incubation period, cause the cells of interest to release analyte that is captured by the capture elements on the capture beads.

Optionally, the substrate may include a hydrophobic layer disposed thereon. The hydrophobic layer may be formed on the droplet operations surface. The droplet operations gap may be configured to retain a filler fluid including the sample droplet containing the cells of interest. The microwells may have a size and pitch dimensioned to receive only a single cell from the cells of interest in the sample droplet and to receive only a single one of the microbeads. The microwells may have a depth of between 30 µm and 50 µm. The microwells may have a diameter of between 3 µm and 60 µm. The microwells may be spaced from one another by a pitch no greater than 80 µm.

In other embodiments, the microwell device includes a second substrate having a plurality of cell traps that open onto the droplet operations surface of the microwell device. The cell traps are disposed in proximity to the microwells. For example, the second substrate is a top surface of the microwell device, while the microwells are on the bottom surface of the device. In one embodiment, the cell traps on the second substrate are positioned directly above the microwells on the first substrate. The sample droplet includes cells of interest that enter the cell traps. The method introduces capture beads to the microwells, and the capture elements are immobilized on the capture beads. The method utilizes the droplet actuator to transport a cell lysis reagent droplet to the microwell device.

In some embodiments are contemplated methods for capturing cells of interest in a digital microfluidic system, the method comprising: (a) utilizing a droplet actuator to transport a sample droplet to a microwell device, the microwell device including a first substrate having a plurality of microwells that open onto a droplet operations surface of the microwell device, and a plurality of cell traps that open onto the droplet operations surface of the microwell device, the sample droplet including cells of interest that enter the cell traps; (b) introducing capture beads to the microwells, wherein capture elements are immobilized on the capture beads; and (c) utilizing the droplet actuator to transport a cell lysis reagent droplet to the microwell device, wherein portions of the cell lysis reagent droplet enter the microwells and cell traps and, during an incubation period, cause the cells of interest to release analyte that is captured by the capture elements on the capture beads.

In some embodiments, the capture beads are sized such that only one of the capture beads fits in one of the microwells. In other embodiments, the cell traps are sized such that only one of the cells of interest fits in one of the cell traps. In other embodiments, the methods further comprise: (d) during and/or prior to the incubation period, utilizing the droplet actuator to transport a fluid immiscible with the cell lysis reagent droplet to the microwell device, wherein the immiscible fluid does not enter the microwells and cell traps, thereby encapsulating single beads with single cells with cell lysis reagent. In some embodiments, the method further comprises removing the capture beads with the analyte captured thereon from the microwells. In some embodiments, the removing operation includes positioning a magnet proximate to the microwells to form a magnetic field that pulls the capture beads from the microwells. In some embodiments, the methods further comprise utilizing a magnetic field to move the capture beads to and away from the microwells. In some embodiments, each of the capture beads includes a plurality of the capture elements. In some embodiments, the plurality of capture elements include a capture sequence and a unique barcode sequence, wherein the capture sequence is optionally one of i) a poly-T sequence for capture of total mRNA, or ii) a plurality of transcript-specific capture sequences that target a panel of genes of interest.

BRIEF DESCRIPTION OF THE DRAWINGS

FIG. 3A illustrates an example of a process of fabricating the microwells shown in FIGS. 1 and 2 in accordance with embodiments herein.

FIG. 3B illustrates an example of a process of fabricating the microwells shown in FIGS. 1 and 2 in accordance with embodiments herein.

FIG. 3C illustrates an example of a process of fabricating the microwells shown in FIGS. 1 and 2 in accordance with embodiments herein.

FIG. 3D illustrates an example of a process of fabricating the microwells shown in FIGS. 1 and 2 in accordance with embodiments herein.

FIG. 11A illustrates perspective views of a micro-channel device and shows a process of capping an array of microwells with an immiscible phase to form isolated reaction compartments in accordance with embodiments herein.

FIG. 11B illustrates perspective views of a micro-channel device and shows a process of capping an array of microwells with an immiscible phase to form isolated reaction compartments in accordance with embodiments herein.

FIG. 11C illustrates perspective views of a micro-channel device and shows a process of capping an array of microwells with an immiscible phase to form isolated reaction compartments in accordance with embodiments herein.

FIG. 11D illustrates perspective views of a micro-channel device and shows a process of capping an array of microwells with an immiscible phase to form isolated reaction compartments in accordance with embodiments herein.

FIG. 11E illustrates perspective views of a micro-channel device and shows a process of capping an array of microwells with an immiscible phase to form isolated reaction compartments in accordance with embodiments herein.

FIG. 18A provides a side view of the device where beads and cells are co-localized. Open rectangles are cell trapping structures affixed to the top lid, light grey dots are cells trapped on such structures, and the black dots are beads in microwells on the bottom surface. FIG. 18B illustrates a top view of such a device, showing that the cell trapping structure on top lid co-localizes trapped cells with beads in microwells on the bottom surface.

FIG. 19A illustrates the oil loaded into the microchannel (gray shaded area) surrounds the microwell/cell trap locations but does not fill them, leaving the cell, bead, and droplet medium encapsulated or compartmentalized within a single aqueous microchamber with an oil surround. FIG. 19B illustrates a top view of the oil loaded device, where the oil surrounds the microwell/trap, encapsulating the cell and bead together in an aqueous microchamber.

FIG. 20A is a fluorescent image of 10 um fluorescent microspheres (white circles), used as a proxy for cells to allow visualization, trapped on a device as in FIG. 18. FIG. 20B shows superimposed white light and fluorescent images of the fluorescent particles located on the cell trapping structures. FIG. 20C shows oil flowing into the channel resulting in formation of isolated aqueous droplets that mimic the shape of the trap structures, thus encapsulating the spheres. The gap height between the top and bottom surfaces of the device at the cell trap structures is lower than the gap height in the surrounding spaces, and oil is unable to displace water from these gaps under slow flow rate conditions. FIG. 20D shows isolated aqueous chambers surrounded by oil after flushing oil through the channel. The spheres are encapsulated inside the aqueous droplets.

DETAILED DESCRIPTION OF THE INVENTION

Figure 1A:
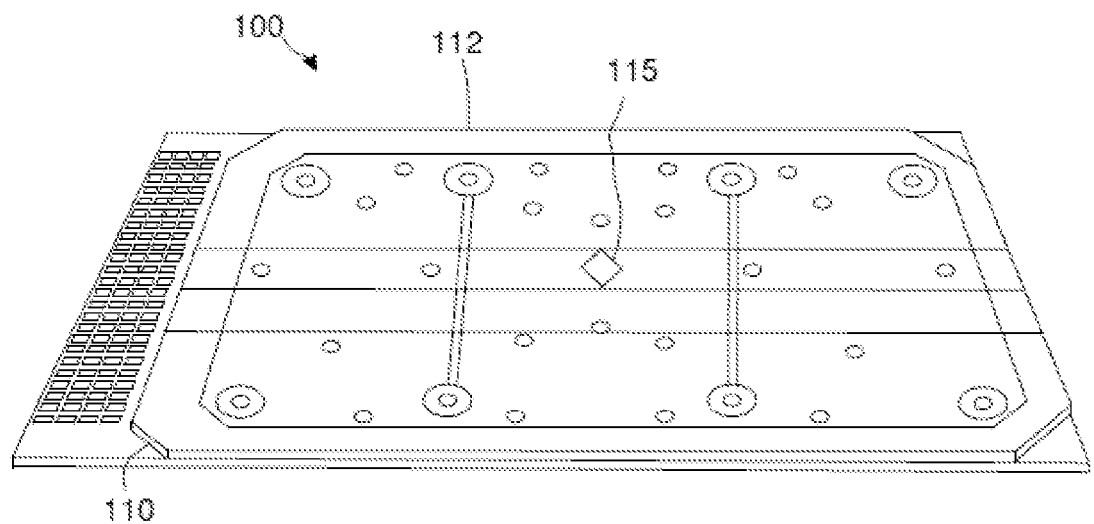
FIG. 1A illustrates a perspective view of an example of a droplet actuator that includes an arrangement of microwells (e.g., an array of microwells) for isolating single cells for characterization of analytes in accordance with embodiments herein.

Embodiments herein provide devices, systems, and methods for isolating single cells for characterization of analytes. In some embodiments, the devices are droplet actuator devices making use of microfluidics technology, such as electrowetting. Devices, systems, and methods of the invention may provide automated liquid handling for processing of biological samples (e.g., cell suspensions) for analysis of analytes. Examples of analytes include nucleic acids (e.g., genomic DNA methylated DNA, mitochondrial DNA, DNA/RNA hybrids, RNA messenger RNA (mRNA), viral RNA, microRNA), proteins, organelles, etc.

In various embodiments, a droplet actuator includes an array of microwells in which multiple single cells are isolated (i.e., a single cell per microwell). The cell may be lysed and analytes from each single cell may be processed. In one embodiment, analytes are captured on one or more capture beads. A capture bead may for example, be a gel bead, or a porous bead, or a hollow bead (e.g., a shell) and may or may not be magnetically responsive. A capture bead may include a barcode that is unique for that capture bead or the capture bead may not include a barcode. A capture bead may be coded in another manner, such as color-coded.

In one embodiment, the array of microwells is formed separately from the droplet actuator and integrated into the bottom substrate of the droplet actuator. The array may be integrated into the droplet operations gap of the droplet actuator. In another embodiment, the array is fabricated directly on a substrate, such as a bottom substrate of a droplet actuator. In one embodiment, the size of a microwell and the size of a capture bead may be selected such that each microwell in the array accommodates a single capture bead.

In one embodiments, a plurality of cell traps is formed separately from the droplet actuator and integrated into the top substrate of the droplet actuator. The plurality of cell traps may be integrated into the droplet operations gap of the droplet actuator. In another embodiment, the plurality of cell traps is fabricated directly onto a substrate, such as a top substrate of a droplet actuator. In one embodiment, the size of the cell trap may be selected such that each trap in the plurality accommodates a single cell.

In various embodiments, a capture bead includes a plurality of capture elements immobilized on the surface of the bead. In one embodiment, the capture elements are capture oligonucleotides immobilized on the surface of a bead for capture of nucleic acids from a single cell. A capture oligonucleotide may, for example, include a nucleic acid capture sequence, a unique molecular identifier (UMI) sequence, and a unique bead-specific barcode sequence. In one example, the nucleic acid capture sequence is a poly-T sequence for capture of total RNA from a single cell. In another example, the nucleic acid capture sequence is a plurality of transcript-specific capture sequences that target a panel of genes of interest. The unique barcode sequence allows each cell's nucleic acids (e.g., transcriptome) to be associated with the original cell. Thus, for any given single cell, genes and transcripts can be identified and assigned to the same cell because the sequences share the same unique barcode. In some embodiments, a capture oligonucleotide also includes a cleavable sequence for releasing captured nucleic acids from the bead.

A droplet actuator of the invention may be configured to perform one or more steps in a sample to analysis protocol. In one embodiment, a droplet actuator may be configured to perform one or more process steps for analysis of nucleic acids. Analysis of the nucleic acids may, for example, include PCR analysis and/or sequencing analysis. In one example, a droplet actuator may be configured to perform one or more steps in a sample to sequencing-ready library protocol. A droplet actuator may be configured for isolation of multiple single cells in individual microwells on the droplet actuator together with single beads in individual microwells, and capture of the nucleic acid from each single cell on a unique barcoded bead. The barcoded beads from each microwell on the droplet actuator are then recovered from the droplet actuator and processed on bench to generate a sequencing-ready library.

In another example, a droplet actuator may be configured for isolation of multiple single cells in individual microwells on the droplet actuator together with single beads in individual microwells, capture of the nucleic acid from each single cells on a unique barcoded bead, and processing of the captured nucleic acid on the droplet actuator to generate a sequencing-ready library.

In another example, a droplet actuator may be configured for isolation of multiple single cells in individual cell traps on the droplet actuator and for isolation of single beads in individual microwells, where each cell trap is positioned proximally to an individual microwell, capture of the nucleic acid from each single cell on a unique barcoded bead, and processing of the captured nucleic acid on the droplet actuator to generate a sequencing-ready library.

Integrated Microwell Device on a Droplet Actuator

A droplet actuator typically includes one or more substrates configured to form a surface or gap for conducting droplet operations. The one or more substrates establish a droplet operations surface or gap for conducting droplet operations and may also include electrodes arranged to conduct the droplet operations. The droplet operations substrate or the gap between the substrates may be coated or filled with a filler fluid that is immiscible with the liquid that forms the droplets.

FIG. 1A illustrates a perspective view of an example of a droplet actuator 100 that includes an arrangement of microwells (e.g., an array of microwells) for isolating cells of interest (e.g., single cells) for characterization of analytes. Droplet actuator 100 includes a bottom substrate 110 and a top substrate 112 that are separated by a droplet operations gap. Bottom substrate 110 is, for example, a printed circuit board (PCB). Top substrate 112 is, for example, a plastic or glass substrate. The droplet actuator 100 includes a compartment 113 formed in one or both of the top and bottom substrates 112, 110. The compartment 113 is shaped and dimensioned to receive a microwell device 115. For example, the microwell device 115 is formed separately from bottom substrate 110. Then, microwell device 115 is mated to bottom substrate 110 of droplet actuator 100. In so doing, microwell device 115 is provided in relation to the droplet operations gap of droplet actuator 100. Optionally, the microwell device 115 may be inserted into a compartment in the top substrate 112, or formed integral with one of the top and bottom substrates 112, 110.

In one example, microwell device 115 is about 10.2 mm×9.5 mm in size. Microwell device 115 includes, for example, an array of microwells (not shown).

Figure 1B:
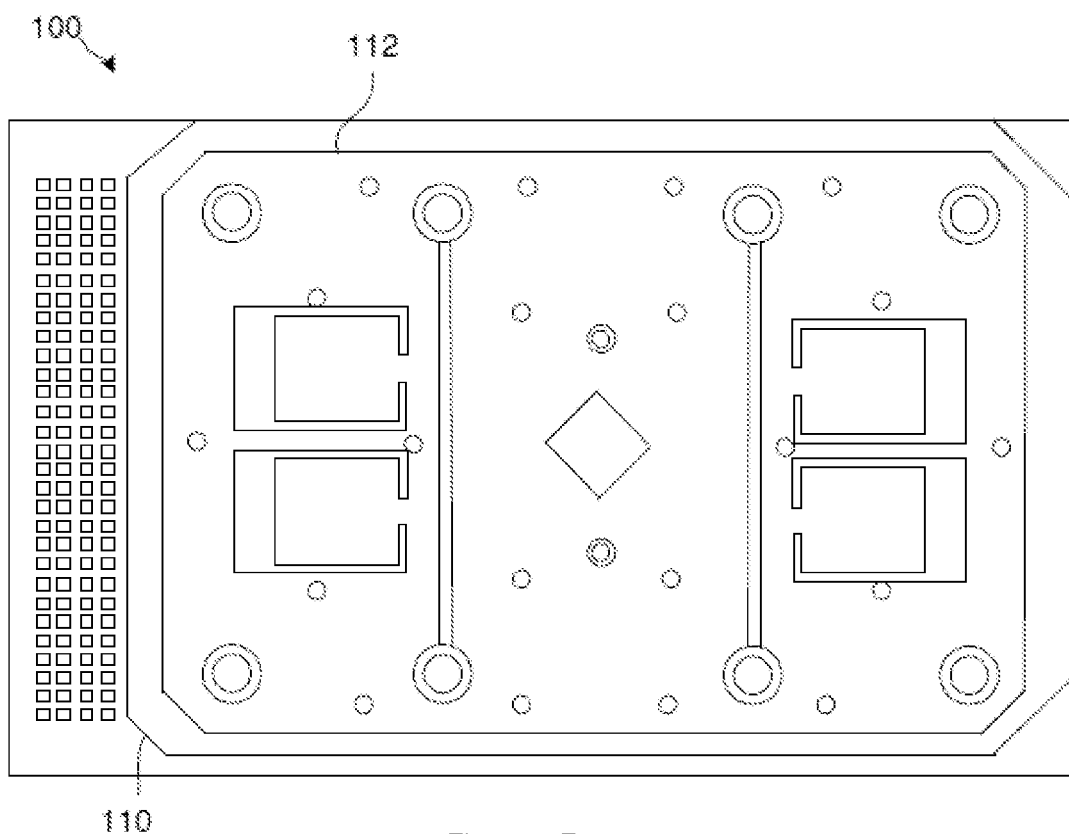
FIG. 1B illustrates a top view of the droplet actuator of FIG. 1A and shows the arrangement of fluid reservoirs for dispensing and/or collecting reaction fluids in accordance with embodiments herein.

FIG. 1B illustrates a top view of droplet actuator 100 of FIG. 1A and shows the arrangement of fluid reservoirs for dispensing and/or collecting reaction fluids. Droplet actuator 100 includes multiple fluid reservoirs 120 (e.g., 4 fluid reservoirs 120a through 120d), which may, for example, be allocated as waste fluid collecting and/or fluid dispensing reservoirs. In this example, fluid reservoir 120a may be used as a sample dispensing reservoir for dispensing one or more sample droplets that include a quantity of single cells of interest; fluid reservoir 120b may be used as a reagent dispensing reservoir for dispensing one or more reagent droplets that include a quantity of capture beads (e.g., barcoded magnetically responsive capture beads); fluid reservoir 120c may be used as a reagent dispensing reservoir for dispensing one or more cell lysis buffer droplets; and fluid reservoir 120d may be used as a waste fluid collecting reservoir for receiving spent reaction droplets. In various embodiments, other reservoirs and reagents may be provided, e.g., a buffer for recovering the capture beads from the microwells after cell lysis and analyte binding as per the step described below with reference to FIG. 5G. Droplet actuator 100 and microwell device 115 are described in more detail with reference to FIG. 2.

Figure 2:
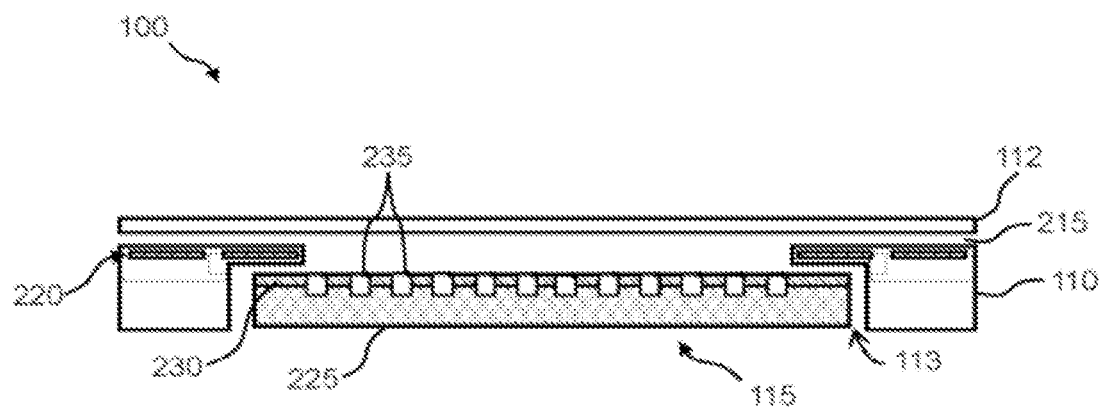
FIG. 2 illustrates a side view of a portion of a microwell device and the droplet actuator of FIG. 1 in accordance with embodiments herein.

FIG. 2 illustrates a side view of a portion of microwell device 115 and droplet actuator 100 of FIG. 1. Bottom substrate 110 is separated from top substrate 112 by a droplet operations gap 215. Droplet operations are conducted in droplet operations gap 215 on a droplet operations surface. The microwell device 1115 is coupled to, and held within, the compartment 113 in a manner that a surface of the microwell device 115 forms a segment of the droplet operations surface. Bottom substrate 110 includes an arrangement of droplet operations electrodes 220 (e.g., electrowetting electrodes). Droplet operations are conducted atop droplet operations electrode 220 on a droplet operations surface. Microwell device 115 integrated in bottom substrate 110 includes a substrate 225. In one example, substrate 225 is a silicon substrate. A hydrophobic layer 230 is disposed on the surface of substrate 225 that is facing droplet operations gap 215. The hydrophobic layer 230 forms a side of the droplet operations gap 215 for the region of the droplet operations gap 215 aligned with the microwell device 115. In on example, hydrophobic layer 230 is formed of CYTOP. A plurality (e.g., an array) of microwells 235 are formed in, and open onto, substrate 225 and hydrophobic layer 230. The microwells 235 open onto the droplet operation surface of the microwell device 115. Fabrication of microwell device 115 is described in more detail with reference to FIGS. 3A through 3D.

A sample droplet (not shown) may be transported using droplet operations along droplet operations electrodes 220 to microwell device 115. In one example, the sample droplet may contain a plurality of cells of interest (e.g., single cells) to be processed for construction of a nucleic acid library for sequencing as described in more details with reference to FIGS. 5A through 5G.

FIG. 3A through 3D illustrate an example of a process 300 of fabricating microwell device 115 of FIGS. 1 and 2. The density of microwells 235 in microwell device 115 is readily tunable by adjusting the size and pitch of microwells 235. In this example, only a portion of microwell device 115 is shown.

In a first step and referring now to FIG. 3A, substrate 225 is provided. In one example, substrate 225 is a silicon wafer that is about 10.2 mm×9.5 mm in size. Then, hydrophobic layer 230 (e.g., CYTOP, FOTS or other fluorinated monolayers or polymers) is formed on the surface of substrate 225.

In a next step and referring now to FIG. 3B, using a standard photolithography process a photoresist layer 310 is provided atop hydrophobic layer 230. Then, an array of circular voids 315 is patterned into photoresist layer 310. In so doing, a shadow mask is formed atop hydrophobic layer 230 that leaves circular regions of hydrophobic layer 230 exposed. This shadow mask is used for defining the location of and etching microwells 235.

The diameter of each of the circular voids 315 can be, for example, from about 3 μm to about 60 μm. In one example, the diameter of each of the circular voids 315 is about 40 μm and the pitch of the circular voids 315 is about 80 μm. In this example, the density of circular voids 315 on substrate 225 is about 150 circles/mm.sup.2. Accordingly, about 15,000 circular voids 315 can be provided in an area of about 10.2 mm×9.5 mm. The size of circular voids 315 is selected based on the size of a microbead that is used in a bead-based protocol for capture of targeted analytes (e.g., nucleic acids).

In a next step and referring now to FIG. 3C, an etching process is used to remove material from the portions of hydrophobic layer 230 and substrate 225 that are exposed through circular voids 315 in photoresist layer 310 and thereby form microwells 235. In one example, the etching process is a reactive-ion etching (RIE) process. At circular voids 315, microwells 235 can be etched to a depth of, from example, from about 30 μm to about 50 μm. In one example, microwells 235 are etched to a depth of about 30 μm. The depth of microwells 225 is selected such that only one microbead and one single cell may fit in any one microwell 225.

In a next step and referring now to FIG. 3D, photoresist layer 310 is removed to expose the portion of the hydrophobic layer 230 that is remaining outside of microwells 225. For example, photoresist layer 310 is removed using an acetone stripping protocol. Microwell device 115 may be described as having a "semi-hydrophobic" surface, i.e., the surfaces of microwells 225 are hydrophilic, while the interstitial regions between microwells 225 are coated with hydrophobic layer 230.

Figure 4:
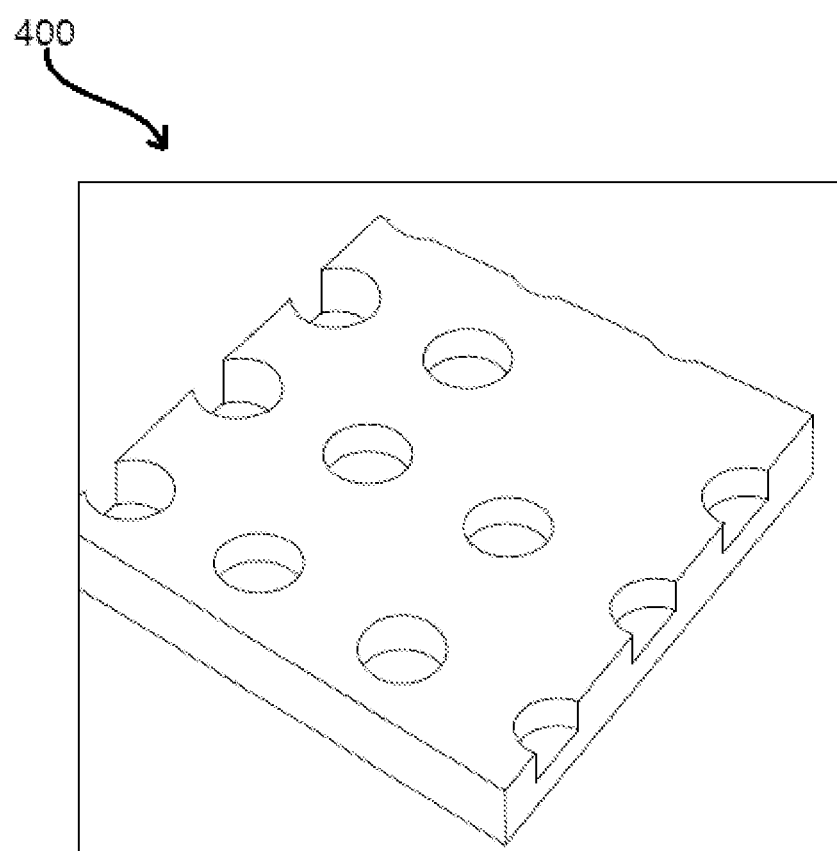
FIG. 4 shows a photo of a portion of a microwell device.

FIG. 4 shows a section 400 of a portion of a microwell device, such as microwell device 115. In this example, the microwells are about 40 μm in diameter on a pitch of about 80 μm.

Single Cell Isolation and Analyte Capture on a Droplet Actuator

FIGS. 5A through 5G illustrate side views of droplet actuator 100 of FIG. 2 and show a process 500 of using a microwell device (e.g., microwell device 115) to isolate single cells for characterization of an analyte. The method FIGS. 5A through 5H is an example of a protocol wherein single cells are isolated in microwells, lysed and a targeted analyte is captured onto beads for subsequent processing. In one example, the capture beads are barcoded beads that are magnetically responsive and the targeted analyte is RNA. Process 500 may include, but is not limited to, the following steps.

Figure 5A:
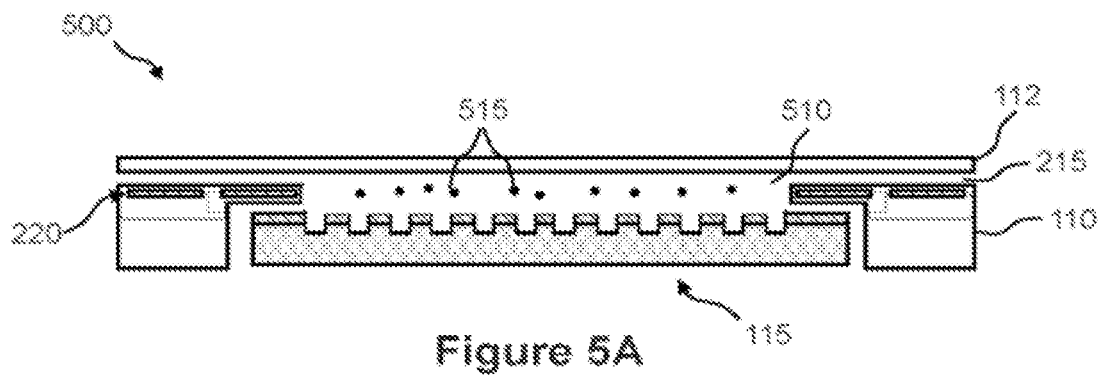
FIG. 5A illustrates side views of the droplet actuator of FIG. 2 and show a process of using a microwell device to isolate single cells for characterization of an analyte in accordance with embodiments herein.

In one step and referring now to FIG. 5A, a sample droplet 510 is transported via droplet operations to microwell device 115. Sample droplet 510 includes a quantity of single cells 515.

Figure 5B:
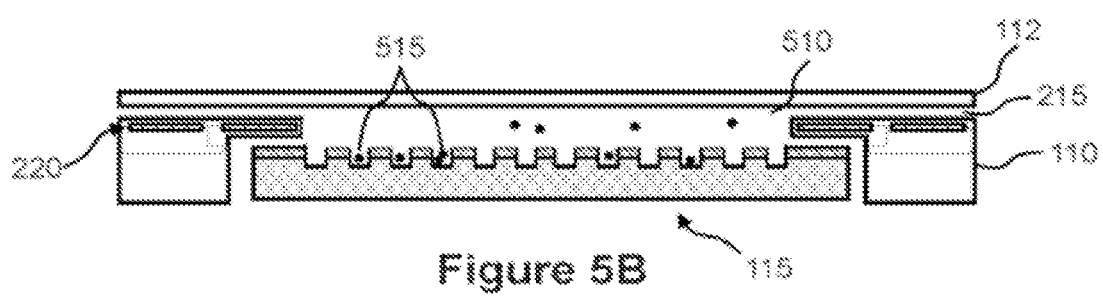
FIG. 5B illustrates side views of the droplet actuator of FIG. 2 and show a process of using a microwell device to isolate single cells for characterization of an analyte in accordance with embodiments herein.

In another step and referring now to FIG. 5B, sample droplet 510 is incubated at microwell device 115 for a period of time (e.g., about 30 to about 60 seconds) that is sufficient for single cells 515 to settle (by gravity) into microwells 235. The capture rate of cells in microwells 235 is a function of the initial concentration of single cells 515 in sample droplet 510 and the amount of time that sample droplet 510 is positioned at microwell device 115.

Figure 5C:
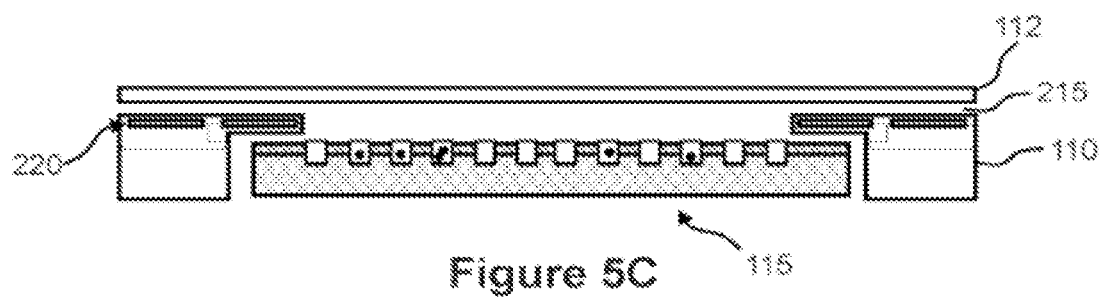
FIG. 5C illustrates side views of the droplet actuator of FIG. 2 and show a process of using a microwell device to isolate single cells for characterization of an analyte in accordance with embodiments herein.

In another step and referring now to FIG. 5C, sample droplet 510 is transported using droplet operations away from microwell device 115. As sample droplet 510 is transported away from microwell device 115, residual sample fluid and single cells 515 captured in microwells 235 are retained at microwell device 115. Because of the presence of hydrophobic layer 230 in the interstitial region between microwells 235, residual sample liquid and cells are localized in microwells 235 and the interstitial area is substantially free of sample residue.

Figure 5D:
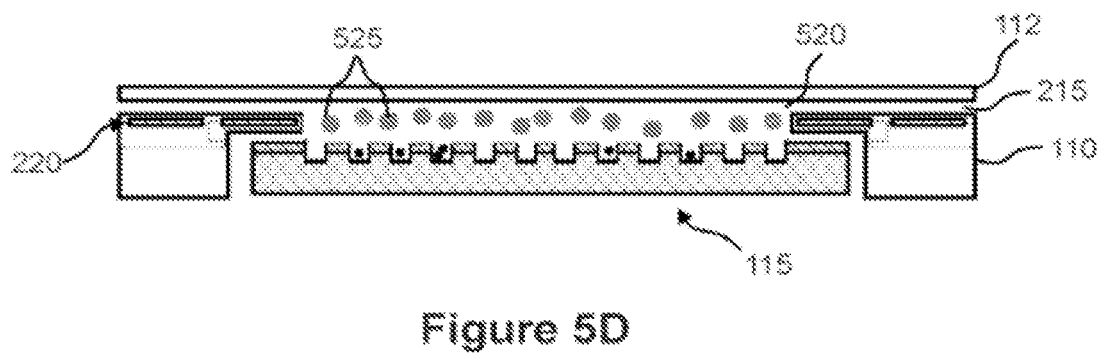
FIG. 5D illustrates side views of the droplet actuator of FIG. 2 and show a process of using a microwell device to isolate single cells for characterization of an analyte in accordance with embodiments herein.

In another step and referring now to FIG. 5D, a reagent droplet 520 that includes a quantity of magnetically responsive capture beads 525 is transported using droplet operations to microwell device 115. Immobilized on each magnetically responsive capture bead 525 is a plurality of capture elements (e.g., nucleic acid capture probes (not shown)) that include a capture sequence and a unique barcode sequence (not shown). In one example, the capture sequence is a poly-T sequence for capture of total mRNA. In another example, the capture sequence is a plurality of transcript-specific capture sequences that target a panel of genes of interest. The magnetically responsive capture beads 525 are deposited, for example, in microwells 235 by gravity. In another example, a magnet (not shown) may be positioned below microwell device 115 such that the magnetic force of the magnet attracts magnetically responsive capture beads 525 into microwells 235. The concentration of magnetically responsive capture beads 525 in reagent droplet 520 is sufficiently high such that each microwell 235 in microwell device 115 contains a magnetically responsive capture bead 525. The size of magnetically responsive capture beads 525 is such that only one bead will fit in a microwell 235.

Figure 5E:
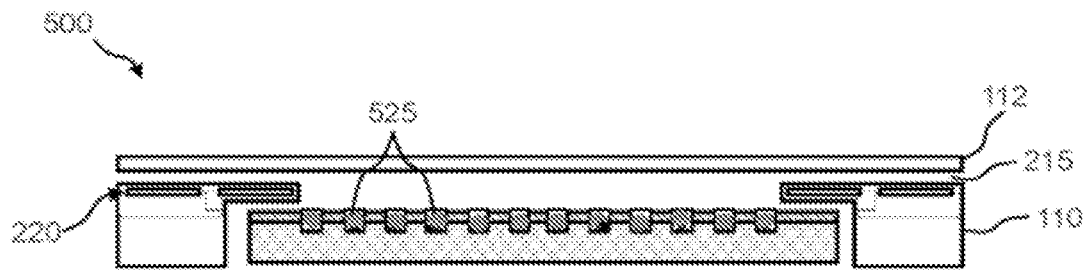
FIG. 5E illustrates side views of the droplet actuator of FIG. 2 and show a process of using a microwell device to isolate single cells for characterization of an analyte in accordance with embodiments herein.

In another step and referring now to FIG. 5E, reagent droplet 520 is transported using droplet operations away from microwell device 115. As reagent droplet 520, which contains any surplus magnetically responsive capture beads 525, is transported away from microwell device 115, residual reagent fluid and magnetically responsive capture beads 525 in microwells 235 are retained at microwell device 115.

Figure 5F:
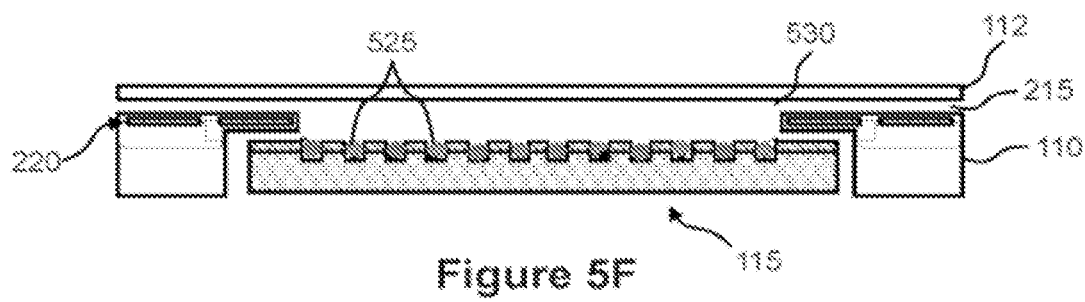
FIG. 5F illustrates side views of the droplet actuator of FIG. 2 and show a process of using a microwell device to isolate single cells for characterization of an analyte in accordance with embodiments herein.

In another step and referring now to FIG. 5F, a cell lysis reagent droplet 530 is transported using droplet operations to microwell device 115. Cell lysis reagent droplet 530 is then transported using droplet operations away from microwell device 115. Each microwell 235 now includes a quantity of cell lysis reagent and a magnetically responsive capture bead 525. Some microwells 235 may include one single cell 515. Other microwells 235 may include more than one (e.g. two) single cells 515. In an incubation period (e.g., from about 10 minutes to about 15 minutes), single cells 515 are lysed in microwells 235 and the released analyte (e.g., RNA) is captured on magnetically responsive capture beads 525.

Figure 5G:
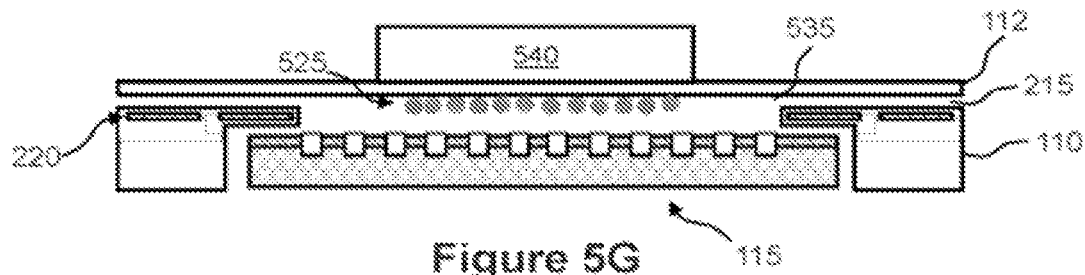
FIG. 5G illustrates side views of the droplet actuator of FIG. 2 and show a process of using a microwell device to isolate single cells for characterization of an analyte in accordance with embodiments herein.

In another step and referring now to FIG. 5G, a capture droplet 535 is transported using droplet operations to microwell device 115. A magnet 540 is positioned above top substrate 112 and aligned with microwell device 115 such that microwell device 115 is within the magnetic field thereof. The magnetic field of magnet 540 is used to pull magnetically responsive capture beads 525 with captured analyte (e.g., RNA (not shown)) thereon out of microwells 235 and into capture droplet 535.

Figure 5H:
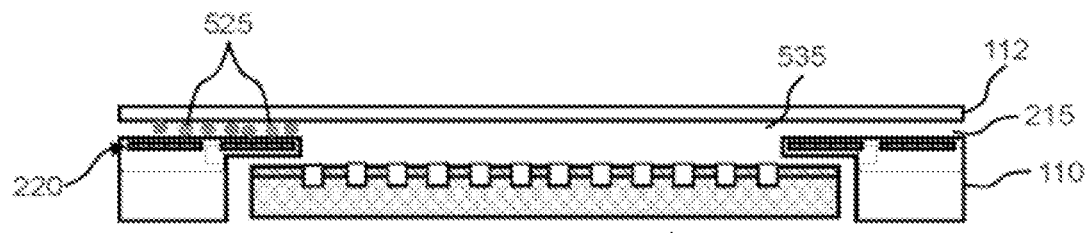
FIG. 5H illustrates side views of the droplet actuator of FIG. 2 and show a process of using a microwell device to isolate single cells from characterization of an analyte in accordance with embodiments herein.

In another step and referring now to FIG. 5H, magnet 540 is moved away from microwell device 115 and top substrate 112. As magnet 540 is moved away from microwell device 115, magnetically responsive capture beads 525 with captured analyte (e.g., RNA) thereon are suspended in capture droplet 535. Then, capture droplet 535 with magnetically responsive capture beads 525 therein is transported using droplet operations away from microwell device 115 for subsequent processing steps (e.g., reverse transcription of RNA to cDNA, PCR amplification, library preparation, and sequencing).

In one example, capture droplet 535 with magnetically responsive capture beads 525 therein is removed from droplet actuator 100 and the subsequent processing steps (e.g., sample clean-up, reverse transcription of RNA to cDNA, PCR amplification, library preparation (e.g., Nextera protocol), and sequencing) are performed off the droplet actuator.

In another example, the subsequent processing steps (e.g., sample clean-up, reverse transcription of RNA to cDNA, PCR amplification, and library preparation) are performed on the droplet actuator to generate a sequencing-ready library. The sequencing-ready library is removed from the droplet actuator for subsequent sequencing.

Figure 6A:
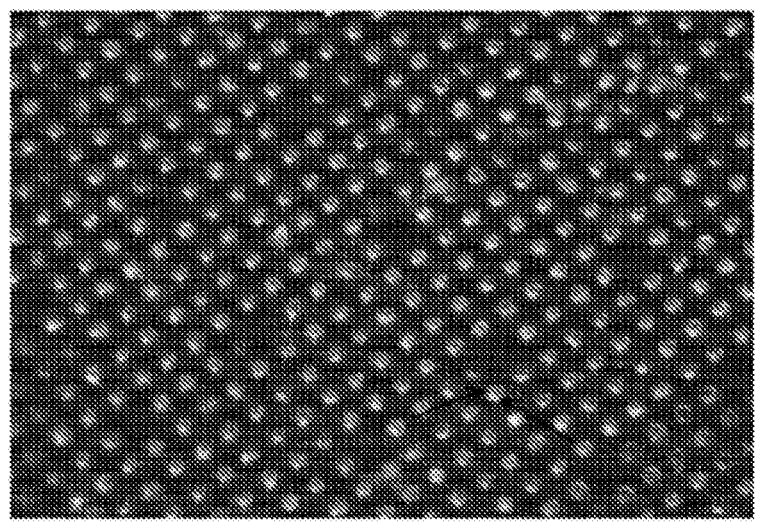
FIG. 6A is a top view of a portion of a microwell device of a droplet actuator that shows co-encapsulation of cells and capture beads in the microwells in accordance with embodiments herein.

FIG. 6A is a top view of a portion of a microwell device 600 of a droplet actuator that shows co-encapsulation of cells and capture beads in the microwells. In this example, the microwells in microwell device 600 are about 30 μm in diameter (250 microwells/mm.sup.2). The capture beads are magnetically responsive beads that are about 20 μm in diameter. Cells are shown in red and the capture beads are shown in green. The cells and capture beads are localized in the microwells of microwell device 600. In this example, where the size of a capture bead is smaller than the size of a microwell, over about 95% of the microwells contain a bead. Because the surface of microwell device 600 is hydrophobic, no residue of cells and/or beads is observed on the surfaces between the microwells.

Figure 6B:
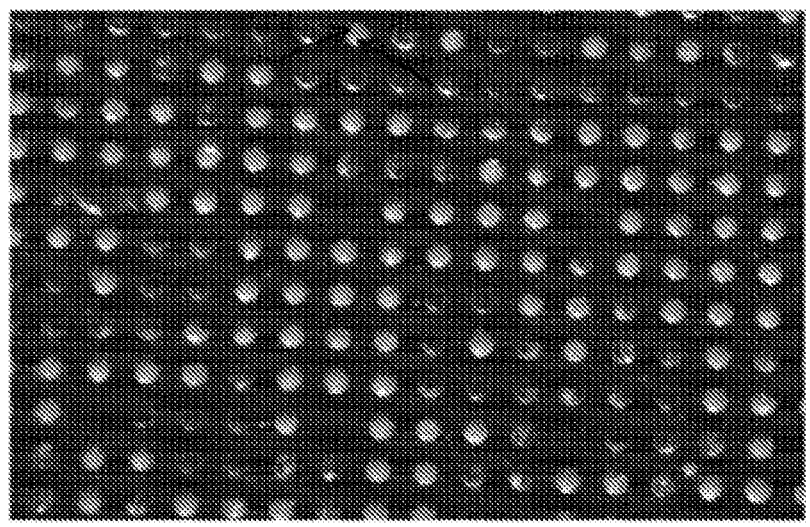
FIG. 6B is a top view of a portion of a microwell device of another droplet actuator that shows co-encapsulation of cells and capture beads in the microwells in accordance with embodiments herein.

FIG. 6B is a top view of a portion of a microwell device 650 of another droplet actuator that shows co-encapsulation of cells and capture beads in the microwells. In this example, the microwells in microwell device 650 are about 40 μm in diameter (150 microwells/mm.sup.2) and the capture beads are about 40 μm in diameter. Cells are shown in red and the capture beads are shown in green. The cells and capture beads are localized in the microwells of microwell device 600. In this example, where the size of a capture bead is about the same size of a microwell, a substantial number of microwells do not contain a capture bead.

Cell Capture Efficiency

To evaluate the efficiency of cell capture onto a microwell device of a droplet actuator, two different droplet actuators were used. A first droplet actuator included a microwell device that is 9.2 mm×2 mm in size and includes about 3,000 microwells that are about 40 μm in diameter on a pitch of about 80 μm. A second droplet actuator included a microwell device that is 9.2 mm×10.5 mm in size and includes about 15,000 microwells that are about 40 μm in diameter on a pitch of about 80 μm. Each droplet actuator was placed onto the stage of a microscope to allow visualization and counting of cells. Three sample solutions with different cell concentrations (i.e., 50 cells/μL, 100 cells/μL, and 250 cells/μL) were used. A sample solution was loaded onto a droplet actuator and a sample droplet was transported using droplet operations to the microwell device of the droplet actuator. After a period of time (e.g., about 60 seconds) sufficient for single cells to settle (by gravity) into the microwells of the microwell device, the sample droplet was transported using droplet operations away from the microwell device. As the sample droplet was transported away from the microwell device, residual sample fluid and single cells were retained in the microwells of the microwell device. The cells captured in the microwells were visualized and counted. Table 1 below shows the cell capture data. The data shows that for the same cell concentration (50 cells/µL or 100 cells/µL), the percentage of microwells that contained a single cell ("Single cell/microwells") is about the same for the 9.2 mm×2 mm microwell device (i.e., .about.2.2% for 50 cell/µL and .about.3.6% for 100 cell/µL) and the 9.2 mm×10.5 mm microwell device (i.e., .about.2% for 50 cell/µL and .about.4% for 100 cell/µL). The data also shows that as the cell concentration in the sample droplet was increased the cell capture rate was increased, but the number of wells with multiple cells (e.g., two cells per well) was also increased. Multiple cells (e.g., two cells) per microwell may be defined as inter-cell contamination or "cross-talk". The efficiency of single-cell capture may be modulated by selecting the size of the microwell array area, the concentration of cells in the sample droplet, and/or the time duration the sample droplet is incubated on the microwell device.

TABLE 1 Cell capture rate before bead loading

| Microwell array cell/area | Cell concentration | Single cell | Multiple cells | Microwells | Single microwells |
|---|---|---|---|---|---|
| 9.2 mm×2 mm | 50/µL | 68 | 4 | ~3000 | ~2.2% |
|  | 100/µL | 108 | 19 | ~3000 | ~3.6% |
| 9.2 mm×10.5 mm | 50/µL | 218 | 18 | ~15000 | ~2% |
|  | 100/µL | 435 | 80 | ~15000 | ~4% |
|  | 250/µL | 644 | 226 | ~15000 | ~6% |

Library Construction from Captured Single-Cell RNA

Figure 7A:
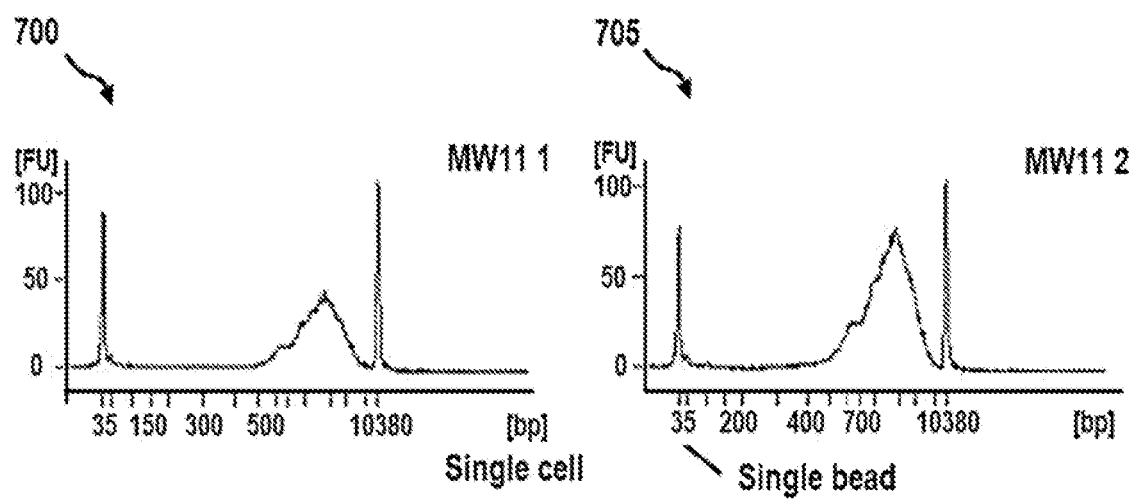
FIG. 7A shows plots of cDNA prepared from RNA recovered from a droplet actuator-based process of capturing single-cell RNA using non-magnetically responsive barcoded beads in accordance with embodiments herein.

FIG. 7A shows a plot 700 and a plot 705 of cDNA prepared from RNA recovered from a droplet actuator-based process of capturing single-cell RNA using non-magnetically responsive barcoded beads. Plot 700 shows the cDNA size distribution from a first fraction (MW11-1) of cDNA bearing beads containing 100 single cells worth of cDNA. Plot 705 shows the cDNA size distribution from a second fraction (MW11-2) of cDNA bearing beads containing 100 single cells worth of cDNA. In this example, a cell sample droplet that contained about 50 cells/4, was loaded onto a droplet actuator and transported using droplet operations to a microwell device on the droplet actuator. After a period of time sufficient for cells in the sample droplet to settle (by gravity) into the microwells of the microwell device, the sample droplet was transported using droplet operations away from the microwell device. A reagent droplet that includes a quantity of non-magnetic barcoded beads was transported using droplet operations to the microwell device. After a period of time sufficient for the barcoded beads to settle (by gravity) into the microwells of the microwell device, the reagent droplet was transported using droplet operations away from the microwell device. A lysis reagent droplet (e.g., a 1% LDS lysis buffer droplet) was transported using droplet operations to the microwell device. After a cell lysis incubation period (e.g., about 15 min), the lysis reagent droplet was transported using droplet operations away from the microwell device. After removal of the lysis reagent droplet, the droplet actuator cartridge was opened and a hybridization buffer solution (e.g., 6×SSC) was pipetted onto the microwell device. The non-magnetic barcoded beads with RNA bound thereon were then removed by pipetting from the microwell device of the droplet actuator for subsequent processing into cDNA using an on-bench reverse transcription protocol. The data show that RNA from lysed cells was captured on the barcoded beads and was readily reverse transcribed to cDNA in an on-bench reaction.

Figure 7B:
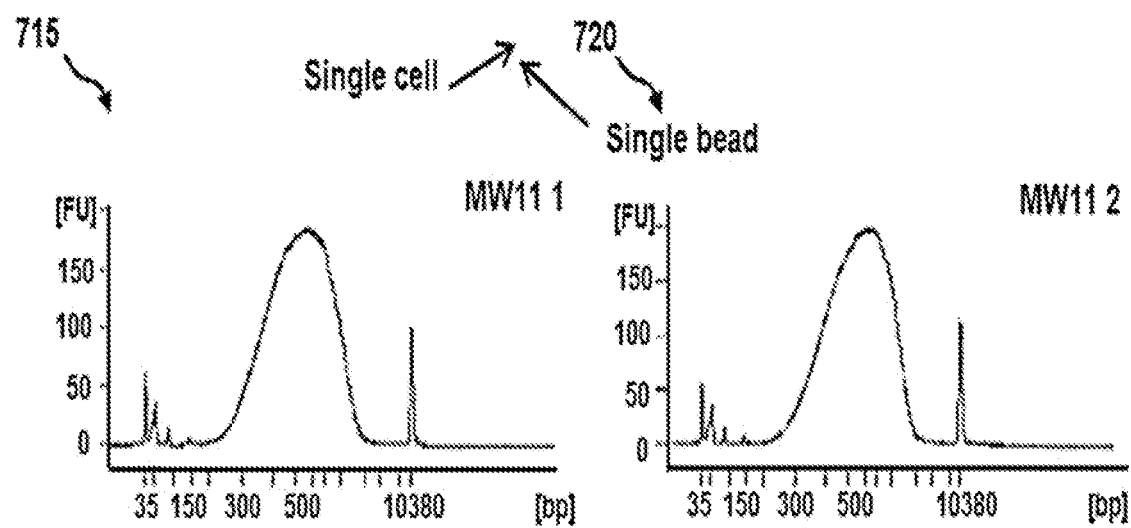
FIG. 7B shows plots of the fragment size distribution of library inserts prepared on-bench from the cDNA of FIG. 7A in accordance with embodiments herein.

FIG. 7B shows a plot 715 and a plot 720 of the fragment size distribution of library inserts prepared on bench from the cDNA of plot 700 and plot 705, respectively, of FIG. 7A. The data show consistent library yield and insert size between the two different library preparation reactions.

Quantification of Cross-Talk

Multiple cells (e.g., two cells) per microwell may be defined as inter-cell contamination or "cross-talk." To quantify cross-talk during single cell isolation and nucleic acid capture on a droplet actuator, a 1-to-1 mixture of human and mouse cells was used. Briefly, the mixed cell sample (50 cells/µL) was loaded on a droplet actuator and transported to a microwell device on the droplet actuator. After a period of time sufficient for single cells to settle (by gravity) into microwells, the mixed sample droplet was transported using droplet operations away from the microwell device. The cells were lysed and the released RNA in each microwell was captured on a unique barcoded bead. The barcoded beads with RNA thereon were recovered from the droplet actuator and the captured RNA was processed for construction of a cDNA library. The cDNA library was sequenced and the transcripts associated with each unique barcode determined. Because human and mouse cells each contain unique transcripts, the transcript and barcode sequence information was used to identify the cell type or cell types associated with each microwell.

Figure 8A:
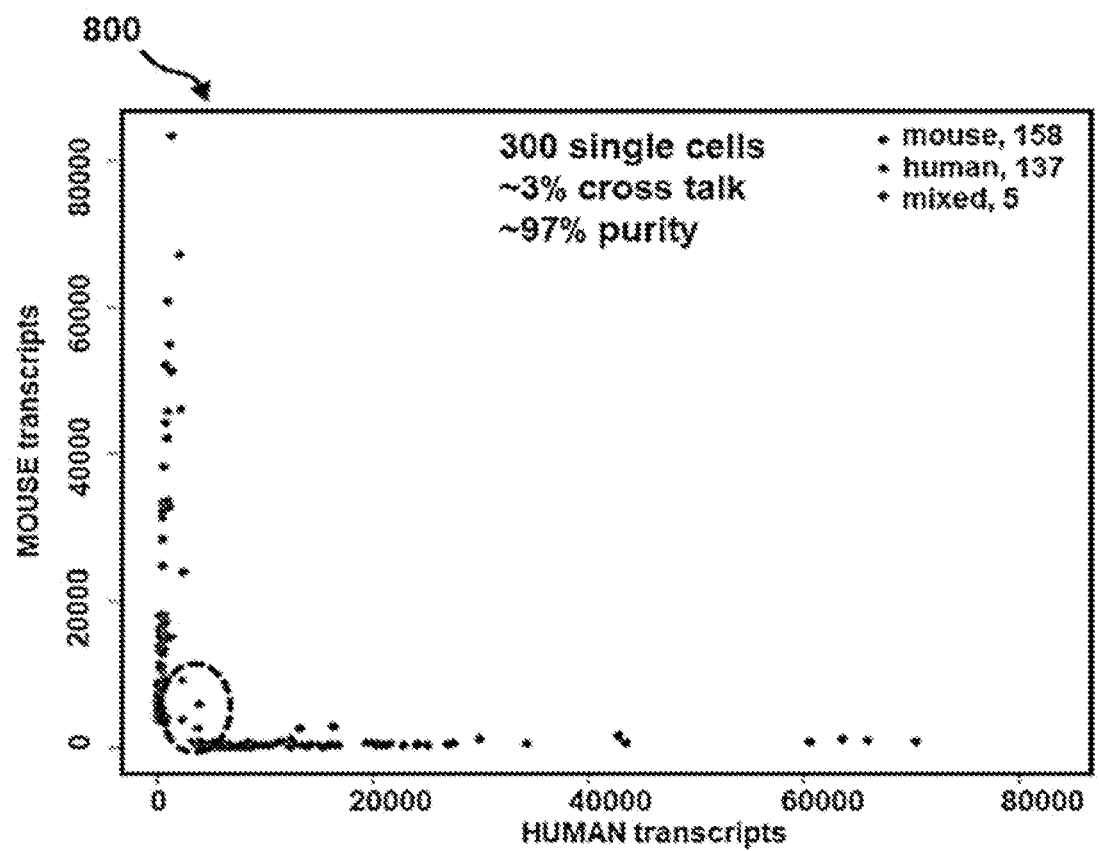
FIG. 8A shows a plot of the read count for human transcripts and mouse transcripts for each unique barcode in accordance with embodiments herein.

FIG. 8A shows a plot 800 of the read count for human transcripts and mouse transcripts for each unique barcode. Each dot on the plot represents a unique barcode, which represents a single well. If a single cell is isolated in a microwell, a transcript associated with a particular barcode will be from either a human cell or from a mouse cell. In the event of cross-talk, e.g., one mouse cell and one human cell per microwell, transcripts from both mouse and human will be associated with a particular barcode. Read counts for human transcripts associated with a particular barcode are plotted on the x-axis. Read counts for mouse transcripts associated with a particular barcode are plotted on the y-axis. The circled area designates reads from both human and mouse cells associated with a particular barcode and indicates cross-talk (i.e., both human and mouse transcripts isolated from the same microwell). In this example, 158 unique barcodes are associated with mouse transcripts, 137 unique barcodes are associated with human transcripts, and 5 unique barcodes are associated with a mix of human and mouse transcripts. The percentage of cross-talk is about 3% and the purity is about 97%.

Figure 8B:
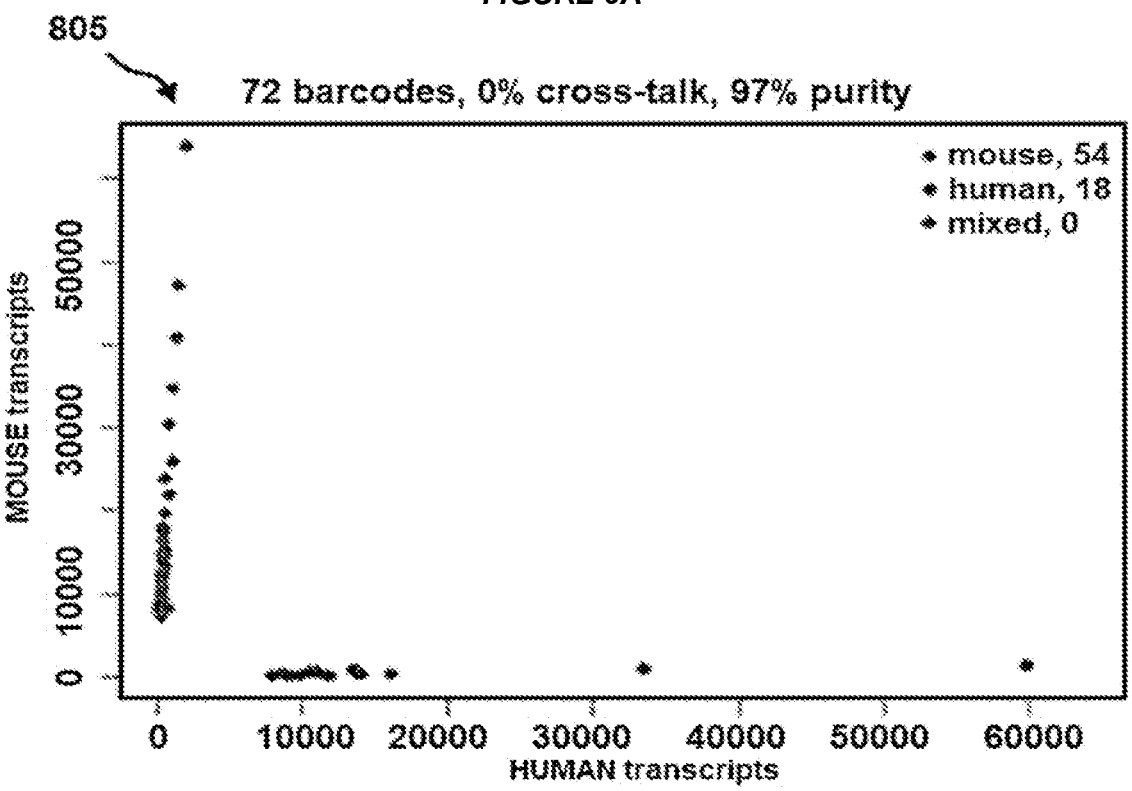
FIG. 8B shows a plot of the read counts for human and mouse transcripts for each unique barcode in a second mixed species experiment in accordance with embodiments herein.

FIG. 8B shows a plot 805 of the read counts for human and mouse transcripts for each unique barcode in a second mixed species experiment. The experiment was performed essentially as described above with reference to FIG. 8A, except that fewer cells were used. In this example, 54 unique barcodes are associated with mouse transcripts, 18 unique barcodes are associated with human transcripts, and 0 unique barcodes are associated with a mix of human and mouse transcripts. The percentage of cross-talk is about 0% and the purity is about 97%. Purity, e.g., 97%, means that on average the mouse associated barcodes contain 97% mouse transcripts and 3% human transcripts; similarly, the human associated barcodes contain 97% human transcripts and 3% mouse transcripts.

Cell Size and Capture Bias

To evaluate the effect of cell size on efficiency of cell capture onto a microwell device of a droplet actuator, two species of cells were used, i.e., human Hek cells and mouse 3T3 cells. An aliquot of each species of cells was stained with a different label and mixed in a 1:1 ratio. The cells were combined into one droplet of around 120 µl and transported onto and then away from the microwell substrate. In the ideal case, the cells are captured in the microwells in a 1:1 ratio due to the initial ratio (e.g., 300 cells captured in microwells, half of them are mouse and the other half are human). However, because of the size of cells, there is a bias. In a similar experiment, two different sizes of beads captured in microwells showed a similar bias, i.e., larger particles are captured at higher rates than smaller particles.

Figure 9:
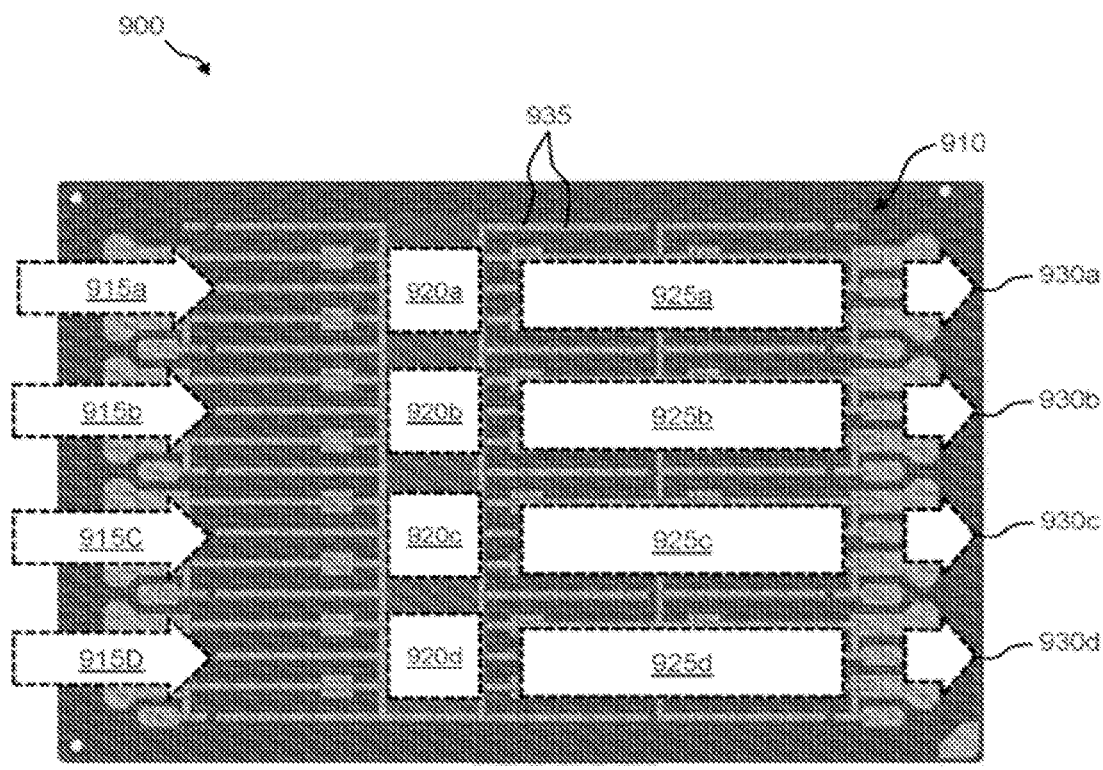
FIG. 9 illustrates a top view of an example of a bottom substrate of a droplet actuator suitable for use in conducting a multiplexed single-cell library construction protocol in accordance with embodiments herein.

Droplet Actuator Configured for Cell Suspension Input to Sequencing Library Output FIG. 9 illustrates a top view of an example of a bottom substrate 900 of a droplet actuator suitable for use in conducting a multiplexed single-cell library construction protocol. Bottom substrate 900 may, for example, be a PCB. Bottom substrate 900 includes an electrode arrangement 910 configured for multiplexed processing of multiple single cells for construction of a one or more single-cell libraries. Droplet operations are conducted atop electrode arrangement 910 on a droplet operations surface. In this example, electrode arrangement 910 is configured for processing up to 4 different samples in parallel in dedicated reaction regions for construction of 4 different single-cell sequencing libraries.

Electrode arrangement 910 includes 4 sample input zones 915 (e.g., sample input zone 915a through 915d) for inputting and dispensing a sample solution (e.g., a single-cell suspension). Electrode arrangement 910 also includes 4 microwell arrays 920 (e.g., microwell array 920a through 920d) configured for isolation of multiple single cells, cell lysis, and capture of nucleic acids (e.g., RNA) on capture beads (e.g., barcoded capture beads). Electrode arrangement 910 also includes 4 reaction zones 925 (e.g., reaction zones 925a through 925d) for performing processing steps for construction of a single-cell library. The processing steps include, for example, reverse transcription of RNA to cDNA, exonuclease I digestion, PCR amplification, and Nextera library preparation. Electrode arrangement 910 also includes 4 library output zones 930 (e.g., library output zone 930a through 930d) for collecting and retrieving library output.

Each sample input zone 915, microwell array 920, reaction zone 925, and library output zone 930 are interconnected through an arrangement, such as a path or array, of droplet operations electrodes 935 (e.g., electrowetting electrodes). For example, sample input zone 915a, microwell array 920a, reaction zone 925a, and library output zone 930a are interconnected through an arrangement of droplet operations electrodes 935. The arrangement of each sample input zone 915, microwell array 920, reaction zone 925, library output zone 930, and droplet operations electrodes 935 provide dedicated regions on bottom substrate 900 for processing 4 different samples.

Fabrication of a Microwell Array on a Droplet Actuator

A microwell array may be fabricated directly on the bottom substrate of a droplet actuator. In one example, the microwell array is formed on a defined area of the bottom substrate of a droplet actuator.

Figure 10A:
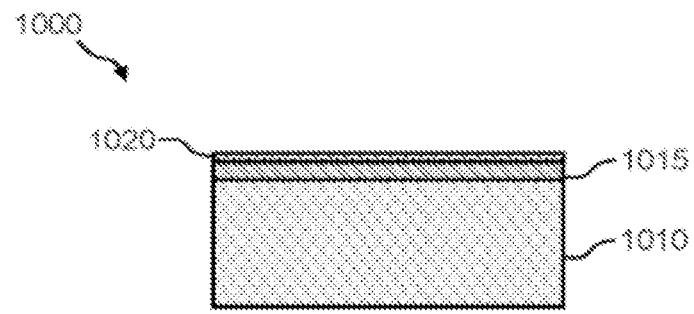
FIG. 10A illustrates an example of a process of fabricating a microwell array on the bottom substrate of a droplet actuator in accordance with embodiments herein.
Figure 10B:
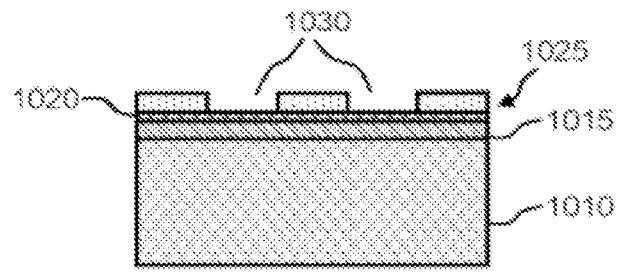
FIG. 10B illustrates an example of a process of fabricating a microwell array on the bottom substrate of a droplet actuator in accordance with embodiments herein.
Figure 10C:
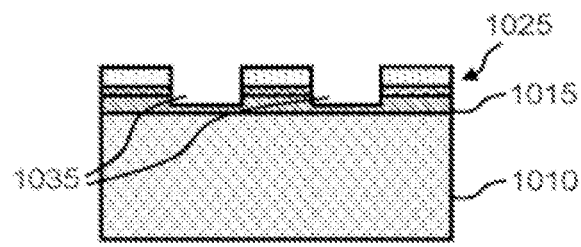
FIG. 10C illustrates an example of a process of fabricating a microwell array on the bottom substrate of a droplet actuator in accordance with embodiments herein.

FIGS. 10A through 10C illustrate an example of a process 1000 of fabricating a microwell array on the bottom substrate of a droplet actuator. Referring now to FIG. 10A, a bottom substrate 1010 is provided. In this example, bottom substrate 1010 is a PCB. The PCB material may be, for example, polyimide with RIE. Atop bottom substrate 1010 is a polyimide layer 1015. In one example, the thickness of polyimide layer 1015 is about 30 µm. Atop polyimide layer 1015 is a hydrophobic layer 1020. In one example, polyimide layer 1015 is a Kapton layer and hydrophobic layer 1020 is a CYTOP layer.

In a first step and referring now to FIG. 10B, a mask 1025 (e.g., photoresist mask) is used to define an array of circular voids 1030. In another example, mask 1025 is a metal mask. In one example, circular voids 1030 are about 50 µm in diameter on a pitch of about 80 µm. The density of circular voids 1030 is about 150 circles/mm.sup.2. In another example, the size range of circular void 1030 is from about 30 µm to about 50 µm in diameter on a pitch range of about 60 µm to about 100 µm. The density range of circular voids 1030 is from about 100 circles/mm.sup.2 to about 1000 circles/mm.sup.2.

In a next step and referring now to FIG. 10C, an etching process is used to remove material from the portions of hydrophobic layer 1020 and polyimide layer 1015 that are exposed through mask 1025 and thereby form microwells 1035. In one example, the etching process is a reactive-ion etching (RIE) process. In this example, microwells 1035 are etched, for example, to a depth of about 2.5 µm.

Figure 10D:
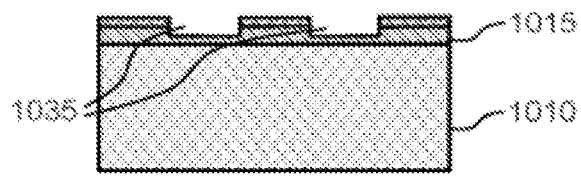
FIG. 10D illustrates an example of a process of fabricating a microwell array on the bottom substrate of a droplet actuator in accordance with embodiments herein.

In a next step and referring now to FIG. 10D, mask 1025 is removed.

In another example, mask 1025 (e.g., a photoresist mask) is replaced with another suitable material (e.g., a metal mask) and an alternative fabrication process is used to form an array of microwells wherein polyimide layer 1015 and bottom substrate 1010 are etched to a total depth of from about 30 µm to about 50 µm.

In another example, polyimide layer 1015 is replaced with a photoimageable material, such as Pyralux™. PC 1000 available from DuPont (Wilmington, Del.). The thickness of the Pyralux™. PC 1000 layer is about 50 µm. A photolithography process is then used to define and develop an array of microwells that are about 50 µm in diameter on a pitch of about 100 µm with a depth of from about 30 µm to about 50 µm. A CYTOP layer (e.g., hydrophobic layer 1020) is then formed on the surface of the remaining surface of the photoimageable layer.

In yet another embodiment, microwells 1035 are formed by imprinting a polymer film layer (e.g., polyimide layer 1015). In one example, the polymer film is Kapton. In another example, the polymer film is a cyclic-olefin. In one example, the imprinting process is a roll-to-roll process that is used to create microwell structures in the polymer substrate.

In yet another embodiment, microwells 1035 are formed in a polymer film layer (e.g., polyimide layer 1015) using a conventional hot embossing process to create microwell structures in the polymer substrate.

In yet another embodiment, microwells 1035 are formed in a resin layer disposed atop a polymer film layer (e.g., polyimide layer 1015). In this example, an imprinting or an embossing process can then be used to create the microwell structures (e.g., microwells 1035). The resin layer is subsequently cured using, for example, a heat or light treatment to create rigid microwell structures on top of the polymer film. Subsequently, the film is laminated onto the digital microfluidic PCB containing electrodes and hydrophobic layer, such as CYTOP, is deposited onto the polymer layer. Yet other processes can be used in the process of forming microwells, such as roll-to-panel processes using thermal-initiated pattern transfer and/or UV-initiated pattern transfer.

Incorporation of Cell-Trapping Structures

In some embodiments, the devices described herein comprise a droplet actuator with one or more substrates configured to form a surface or gap for conducting droplet operations. The one or more substrates establish a droplet operations surface or gap for conducting droplet operations and may also include electrodes arranged to conduct the droplet operations. In some embodiments described herein a microwell device includes a first substrate having a plurality of microwells that open onto a droplet operations surface of the microwell device. In some embodiments, the device further comprises a second substrate comprising a plurality of cell traps that open onto the droplet operations surface of the microwell device. In some embodiments, the cell traps are positioned on the second substrate in close proximity with and open to the microwells on the first substrate. In some embodiments, the cell traps on a top substrate are each positioned above a microwell on the bottom substrate of the device.

Cell traps include structures such as those described in, e.g., Di Carlo, et al., "Dynamic single cell culture array," Lab Chip 2006, 6, 1445-1449, and may be of any suitable shape, such as cup-shaped, U-shaped, or bridge-shaped, or a combination thereof. The cell trap dimensions (width, length, depth) may be optimized readily according to the size of the target cells of interest. Cell traps may be fabricated with any suitable material, such as polydimethylsiloxane (PDMS), and molded onto the second substrate, which may be glass or other suitable material. In some embodiments, the cell traps are arranged in rows that are offset asymmetrically. Molds for trapping array devices may be fabricated using negative photoresists or other suitable methods known in the art.

Figure 18A:
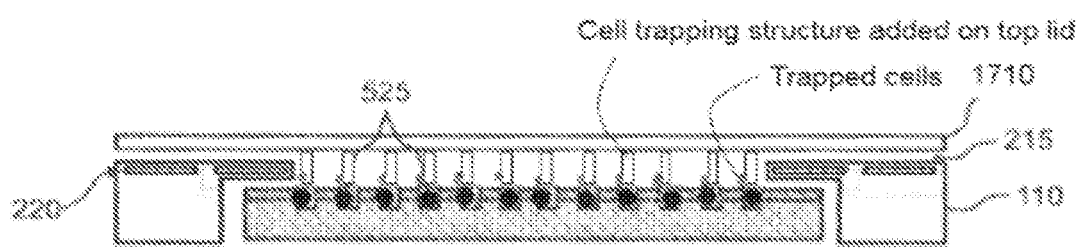
FIGS. 18A-18B illustrate a digital microfluidics device with cell trap structures in the top plate that allow cells of interest to be physically trapped above microwells containing beads.
Figure 18B:
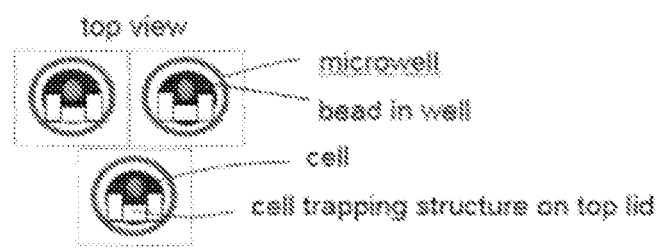

FIGS. 18A-18B illustrate a digital microfluidics device with cell trap structures in a top substrate that allow cells of interest to be physically trapped above microwells in a bottom substrate containing beads. FIG. 18A provides a side view of the device where beads and cells are co-localized. Open rectangles are cell trapping structures affixed to the top substrate 1710, light grey dots are cells trapped on such structures, and the black dots are capture beads 525 in microwells on the bottom substrate 110. Both substrates open onto a droplet operations gap 215. Bottom substrate 110 includes an arrangement of droplet operations electrodes 220 (e.g., electrowetting electrodes). FIG. 18B illustrates a top view of such a device, showing that the cell trapping structure on top substrate serves to co-localize trapped cells with beads in microwells on the bottom substrate.

Sample-Well "Capping" or Encapsulation with an Immiscible Phase

The invention provides micro-channel devices for and methods of compartmentalizing individual reactions in an array of microwells. The micro-channel device includes an array of microwells formed in the floor of a micro-channel such that the micro-channel intersects each microwell along a single edge or face. Each microwell is a reaction compartment that can be filled with an aqueous reaction mixture and then "capped" with an immiscible phase (e.g., oil) such that each microwell (and the contents therein) is isolated from each other microwell. In one embodiment, the reaction mixture includes a quantity of single cells for encapsulation in individual reaction compartments.

FIGS. 11A through 11E illustrate perspective views of a micro-channel device and show a process 1100 of capping an array of microwells with an immiscible phase to form isolated reaction compartments. Process 1100 may include, but is not limited to, the following steps.

In one step and referring now to FIG. 11A, a micro-channel device 1110 includes a micro-channel 1115. Formed in the bottom surface of micro-channel 1115 is a line or array of microwells 1120. In one example, microwells 1120 are circular wells. In another example, microwells 1120 are rectangular in shape.

In other steps and referring now to FIGS. 11B and 11C, a reaction mixture 1125 is flowed into micro-channel 1115, filling micro-channel 1115 and microwells 1120. In one example, reaction mixture 1125 includes a quantity of single cells (not shown) to be encapsulated in individual microwells 1120 for subsequent processing steps. In one example, single cells are encapsulated in individual microwells 1120 for processing in a single-cell genomics protocol. Reaction mixture 1125 is left in micro-channel device 1110 for a period of time that is sufficient for single cells (not shown) to settle (by gravity) into microwells 1120. The capture rate of cells (not shown) in microwells 1120 is a function of the initial concentration of single cells in the reaction mixture and the amount of time that reaction mixture 1125 is retained in micro-channel device 1110.

In other steps and referring now to FIGS. 11D and 11E, an immiscible phase 1130 is loaded into micro-channel 1115. In one example, immiscible phase 1130 is an oil. As immiscible phase 1130 is loaded into micro-channel 1115, reaction mixture 1125 is displaced from micro-channel 1115 and reaction mixture 1125 is retained in microwells 1120. In so doing, microwells 1120 are "capped" with immiscible phase 1130 such that each microwell 1120 is now isolated from all other microwells 1120 and subsequent reactions (e.g., reverse transcription or PCR amplification) is performed in isolated compartments. The reaction products in each microwell 1120 can be recovered, for example, by flowing in and collecting a second aqueous phase solution (not shown).

Figure 12A:
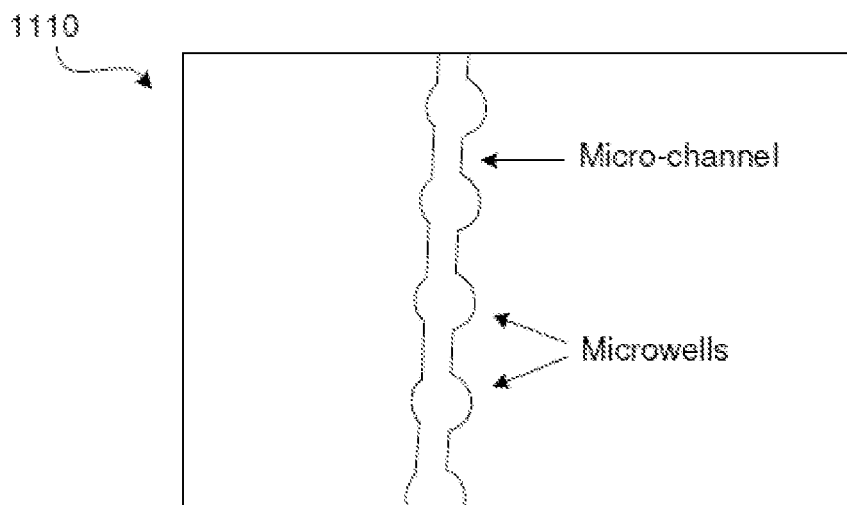
FIG. 12A illustrates a top view of a portion of a micro-channel device that shows a fully loaded micro-channel and associated microwells, and "capped" microwells after oil injection, respectively in accordance with embodiments herein.
Figure 12B:
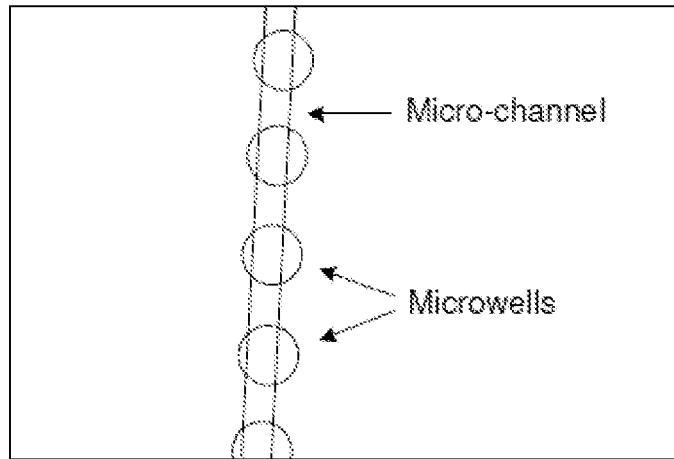
FIG. 12B illustrates a top view of a portion of a micro-channel device that shows a fully loaded micro-channel and associated microwells, and "capped" microwells after oil injection, respectively in accordance with embodiments herein.

FIGS. 12A and 12B are top views of a portion of, for example, micro-channel device 1110 of FIGS. 11A through 11E and showing a fully loaded micro-channel and associated microwells and "capped" microwells after oil injection, respectively.

Figure 13:
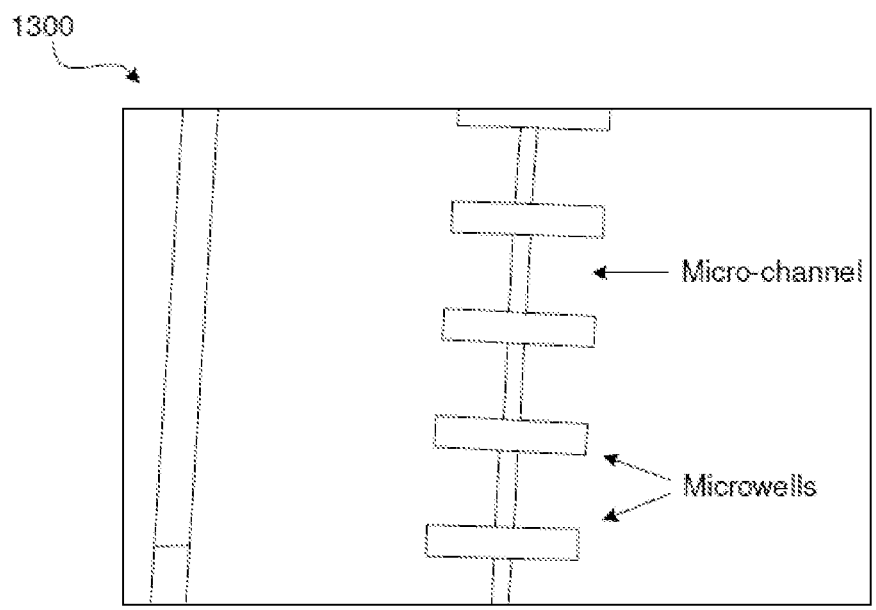
FIG. 13 is a top view of a portion of a micro-channel device 1300 that includes microwells that are rectangular in shape in accordance with embodiments herein.

FIG. 13 is a top view of a portion of a micro-channel device 1300 that includes microwells that are rectangular in shape. In this example, the microwells are filled with an aqueous solution and capped with an immiscible phase (e.g., oil).

Figure 14:
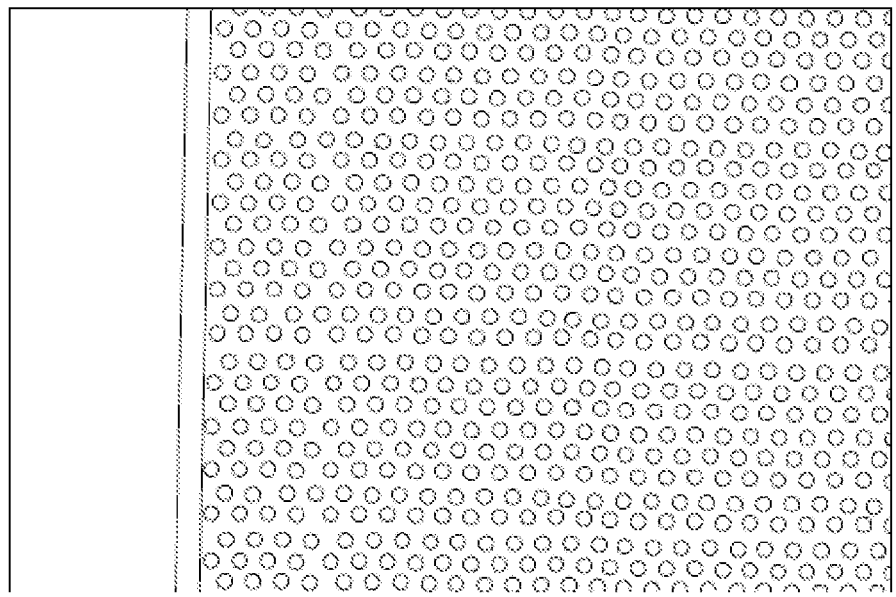
FIG. 14 is a top view of a portion of a highly parallel micro-channel array in accordance with embodiments herein.
Figure 15A:
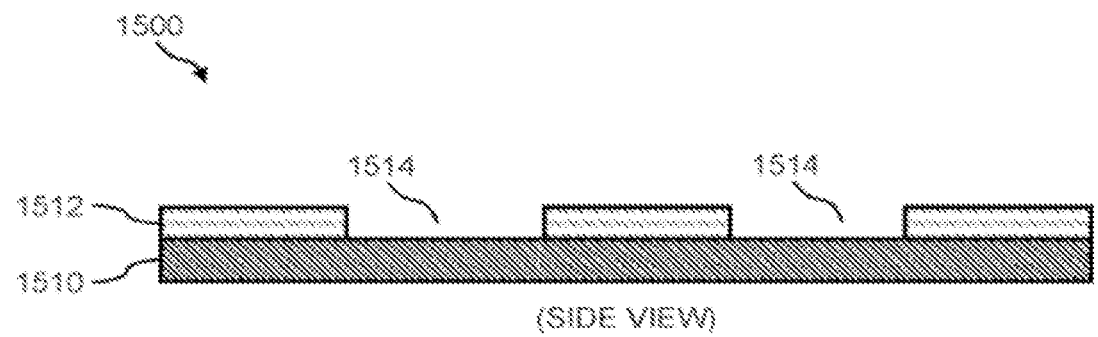
FIG. 15A illustrates an example of a "positive" well structure in accordance with embodiments herein.
Figure 15B:
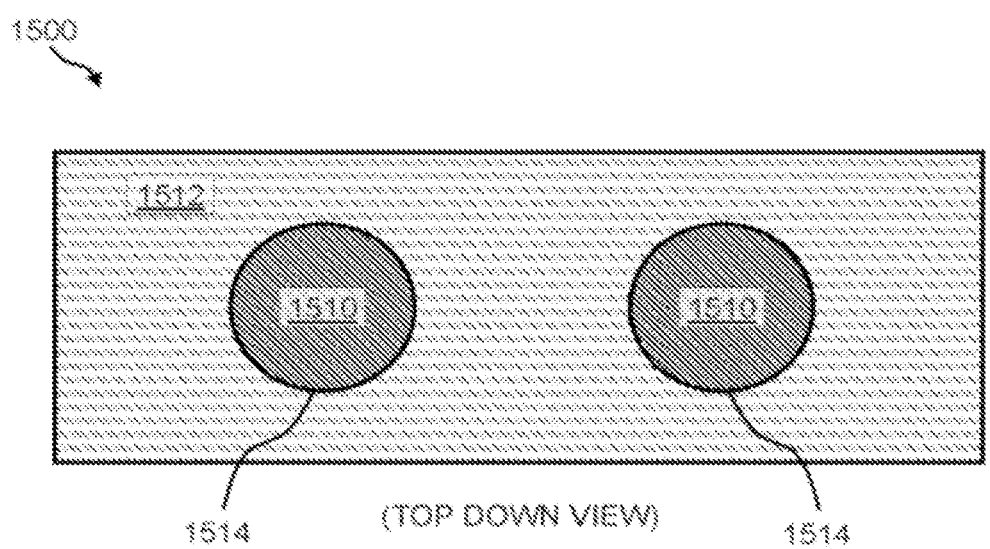
FIG. 15B illustrates an example of a "positive" well structure in accordance with embodiments herein.
Figure 15C:
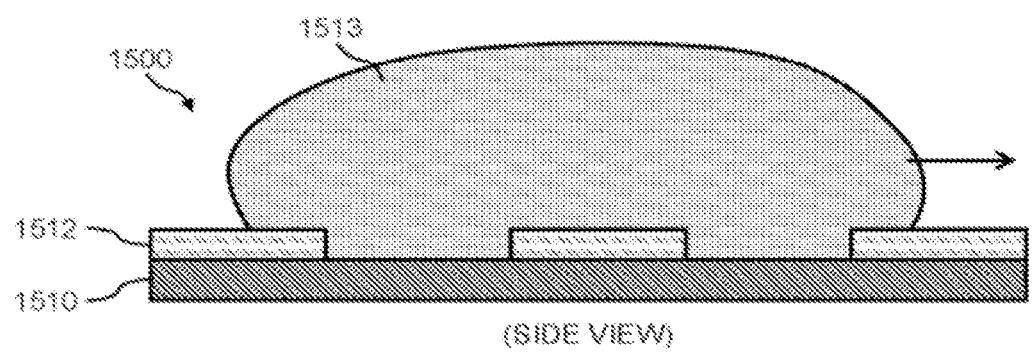
FIG. 15C illustrates an example of a "positive" well structure in accordance with embodiments herein.
Figure 15D:
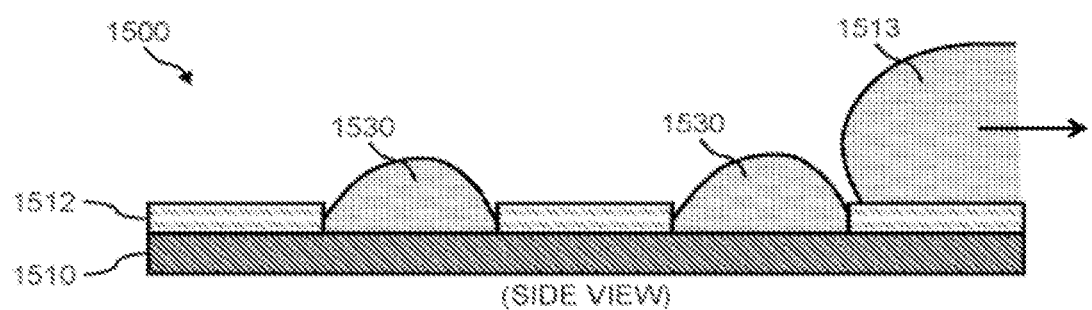
FIG. 15D illustrates an example of a "positive" well structure in accordance with embodiments herein.

FIG. 14 is a top view of a portion of a highly parallel micro-channel array 1400.

Figure 19A:
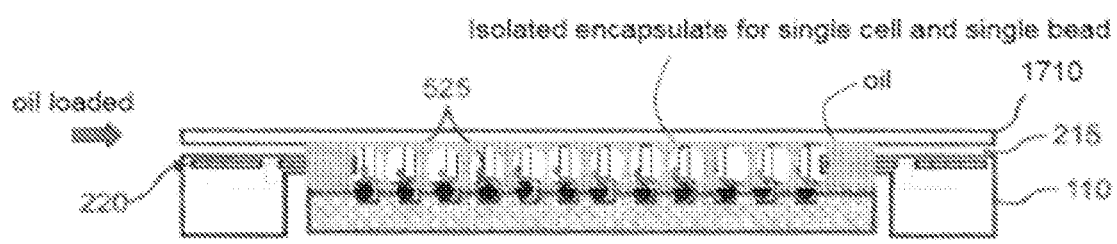
FIGS. 19A-19B illustrate the device of FIG. 18 where oil has been loaded through the channel to displace an aqueous phase droplet and effect encapsulation of bead/cell pairs.
Figure 19B:
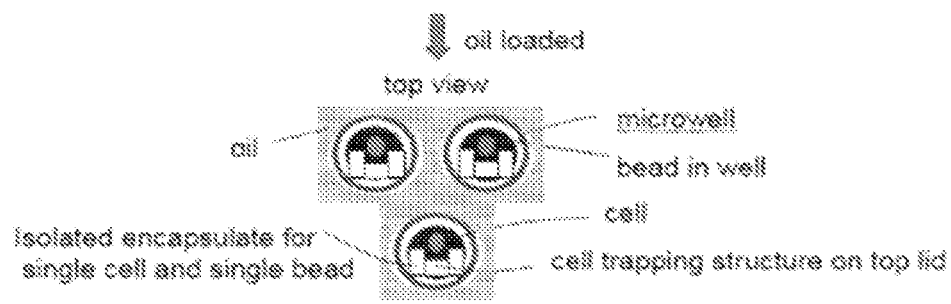

In alternative embodiments, the disclosure provides micro-channel devices for and methods of compartmentalizing individual reactions using an array of microwells in conjunction with an array of cell traps. The micro-channel device includes an array of microwells formed in the floor of a micro-channel such that the micro-channel intersects each microwell along a single edge or face. The micro-channel device includes an array of cell trap structures formed in the ceiling of a micro-channel such that the micro-channel intersects each cell trap along a second edge or face. Each microwell/cell-trap location is a reaction compartment that can be filled with an aqueous reaction mixture and then encapsulated with an immiscible phase (e.g., oil) such that each microwell/cell trap unit (and the contents therein) is isolated from each other microwell/cell trap unit. Once cells and beads have been co-localized in cell traps and microwells, respectively, using, for example, an aqueous medium, an immiscible fluid may be introduced to the system to displace the aqueous medium. The reduced gap between the top and bottom substrates at the location of the microwell/cell trap unit prevents displacement of the aqueous medium at that position. As shown in FIGS. 19A-19B, cells have been loaded into the cell traps on a top substrate 1710 and beads 525 loaded into the microwells on a bottom substrate 110. Oil is loaded through the microchannel 215 to displace an aqueous phase droplet and effect encapsulation of bead/cell pairs. FIG. 19A illustrates that the oil loaded into the microchannel (gray shaded area) surrounds the microwell/cell trap locations but does not fill them, leaving the cell, bead, and aqueous medium encapsulated or compartmentalized within a single aqueous microchamber with an oil surround. FIG. 19B illustrates a top view of the oil loaded device, where the oil surrounds the microwell/trap, encapsulating the cell and bead together in an aqueous microchamber.

Figures 20A, 20B:
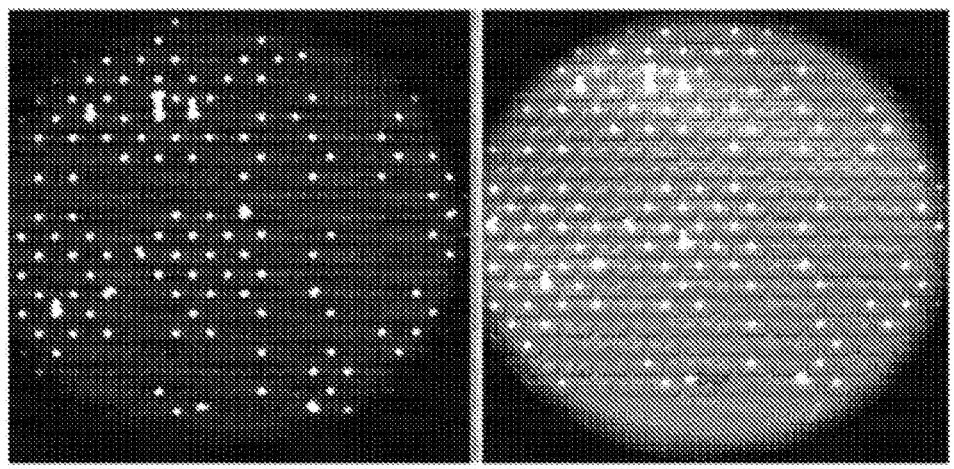
FIGS. 20A-D illustrate trapping and oil encapsulation for spheres trapped on cell trap structures.
Figures 20C, 20D:
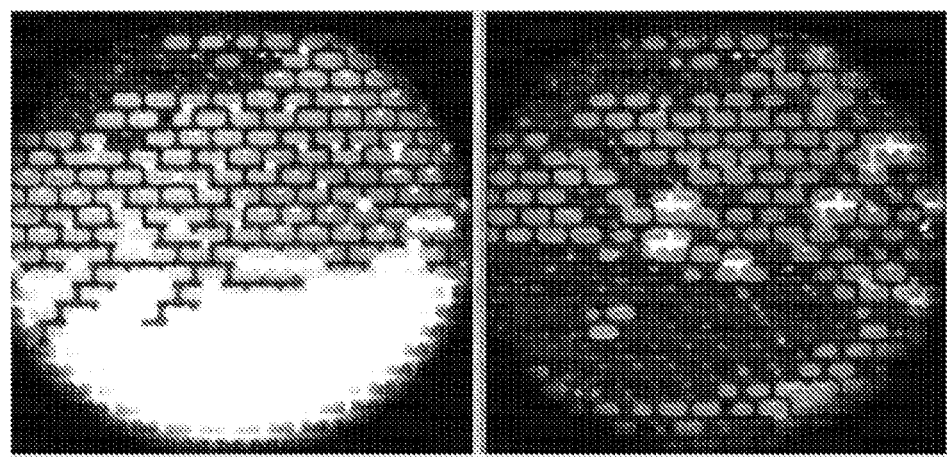

In exemplary embodiments, FIGS. 20A-D illustrate trapping and oil encapsulation for spheres trapped on cell trap structures. FIG. 20A is a fluorescent image of 10 um fluorescent microspheres (white circles), used as a proxy for cells to allow visualization, trapped on a device as in FIG. 18. FIG. 20B shows superimposed white light and fluorescent images of the fluorescent particles located on the cell trapping structures. FIG. 20C shows oil flowing into the channel resulting in formation of isolated aqueous droplets that mimic the shape of the trap structures, thus encapsulating the spheres. The gap height between the top and bottom surfaces of the device at the cell trap structures is lower than the gap height in the surrounding spaces, and oil is unable to displace water from these gaps under slow flow rate conditions. FIG. 20D shows isolated aqueous chambers surrounded by oil after flushing oil through the channel. The spheres are encapsulated inside the aqueous droplets.

"Positive" Wells

FIGS. 15A, 15B, 15C, and 15D show an example of a "positive" well structure 1500. Most of the well designs described above include a geometry which is recessed into the substrate. With the recessed wells, aqueous fluid can be trapped/isolated/compartmentalized either including a surface energy differential (235 vs 230) or without one (1400). In these cases, the bulk of the trapped fluid is at or below the surface of the substrate. However, with a sufficient differential in surface energy, it is also possible to accomplish a similar effect even with a negligible or absent recess (i.e. a "positive" well), where the bulk of the trapped fluid will be at or above the level of the substrate surface.

Positive well structure 1500 includes a hydrophilic layer 1510, such as a layer of glass, silicon oxide, and/or hydrophillically treated polymer. A hydrophobic layer 1512, such as a layer of CYTOP, parylene, and/or FOTS, is atop hydrophilic layer 1510. A void is formed in hydrophobic layer 1512, thereby forming a "positive" well 1514 (i.e., negligible recessed depth but differential surface energy) in which a portion of hydrophilic layer 1510 is exposed. As a larger aqueous droplet or bolus 1513 passes over "positive" well 1514, portions of aqueous droplet or bolus 1513 will remain trapped as smaller isolated volumes 1530 within "positive" well 1514.

Figure 16A:
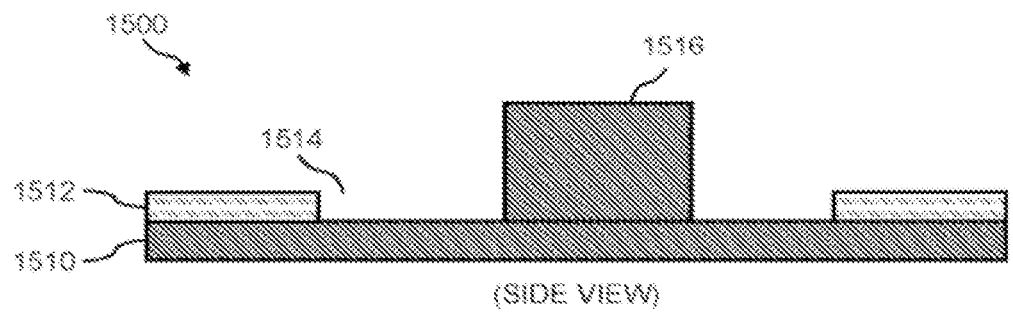
FIG. 16A illustrates another example of a "positive" well structure in accordance with embodiments herein.
Figure 16B:
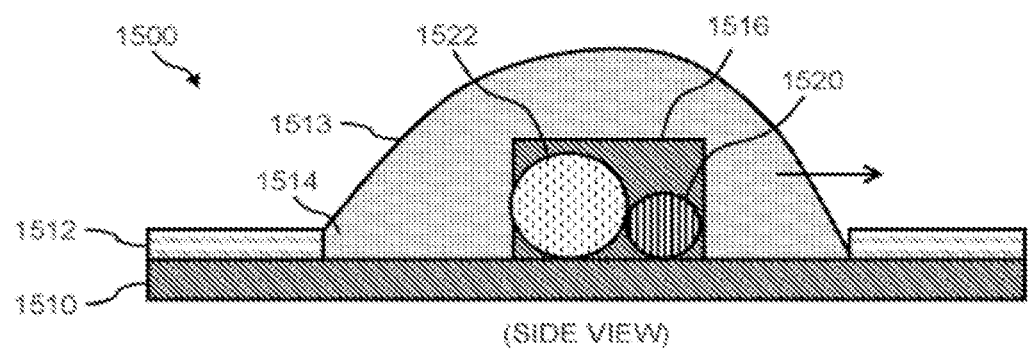
FIG. 16B illustrates another example of a "positive" well structure in accordance with embodiments herein.
Figure 16C:
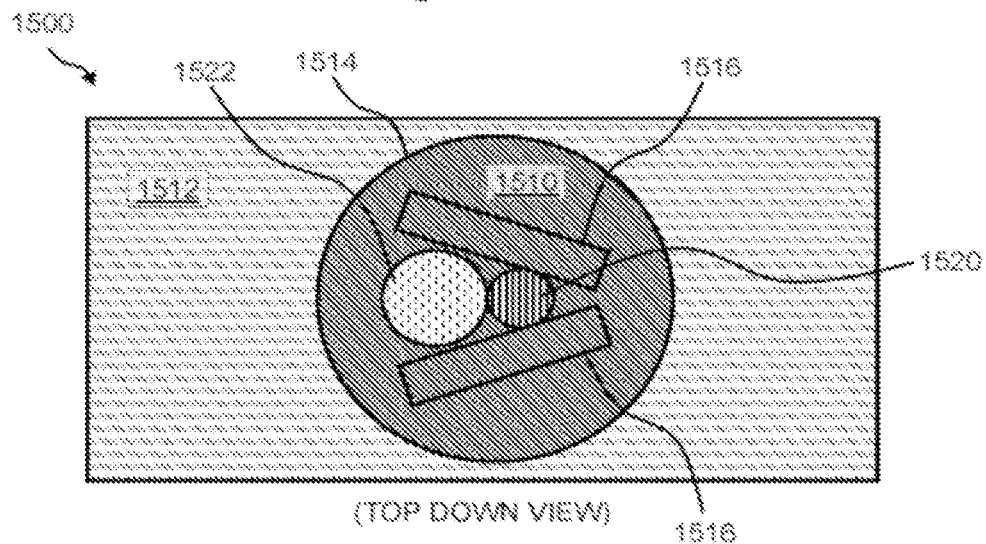
FIG. 16C illustrates another example of a "positive" well structure in accordance with embodiments herein.

Referring now to FIGS. 16A, 16B, and 16C, in order to promote the capture of, for example, a cell 1520 and/or a bead 1522 within "positive" well 1514, the surface of "positive" well 1514 can be coated with chemicals that have an affinity for the cells 1520 and/or beads 1522. Additionally, a pair of hydrophilic trapping features 1516 can be formed atop hydrophilic layer 1510 and within "positive" well 1514. Namely, certain hydrophilic trapping features 1516 can be used to physically trap a cell 1520 and/or a bead 1522 as they are flowed through "positive" well structure 1500. For example, in the case that the loading droplet 1513 contains a plurality of cells 1520 and/or beads 1522 as it flows over "positive" well 1514, either affinity chemistries can bind to cells 1520 and/or beads 1522 keeping them in "positive" well 1514, or hydrophilic trapping features 1516 with an appropriate shape (here shown with a taper smaller than the size of the cell 1520 and/or bead 1522 to be captured) can trap one or more cells 1520 and/or beads 1522 within "positive" well 1514.

Systems

Figure 17:
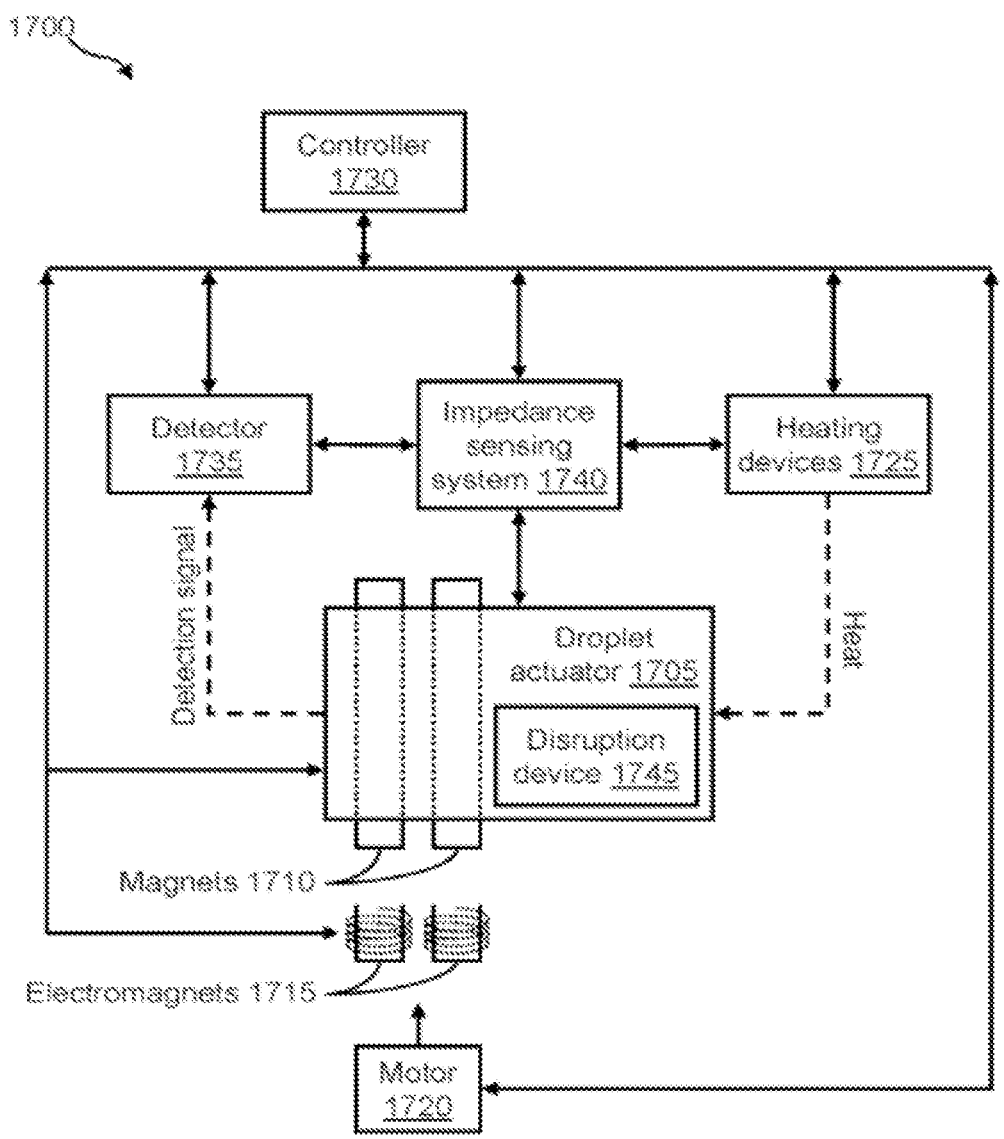
FIG. 17 illustrates a block diagram of an example of a microfluidics system that includes a droplet actuator in accordance with embodiments herein.

FIG. 17 illustrates a functional block diagram of an example of a microfluidics system 1700 that includes a droplet actuator 1705, which is one example of a fluidics cartridge. Digital microfluidic technology conducts droplet operations on discrete droplets in a droplet actuator, such as droplet actuator 1705, by electrical control of their surface tension (electrowetting). The droplets may be sandwiched between two substrates of droplet actuator 1705, a bottom substrate and a top substrate separated by a droplet operations gap. The bottom substrate may include an arrangement of electrically addressable electrodes. The top substrate may include a reference electrode plane made, for example, from conductive ink or indium tin oxide (ITO). The bottom substrate and the top substrate may be coated with a hydrophobic material. Droplet operations are conducted in the droplet operations gap. The space around the droplets (i.e., the gap between bottom and top substrates) may be filled with an immiscible inert fluid, such as silicone oil, to prevent evaporation of the droplets and to facilitate their transport within the device. Other droplet operations may be effected by varying the patterns of voltage activation; examples include merging, splitting, mixing, and dispensing of droplets.

Droplet actuator 1705 may be designed to fit onto an instrument deck (not shown) of microfluidics system 1700. The instrument deck may hold droplet actuator 1705 and house other droplet actuator features, such as, but not limited to, one or more magnets and one or more heating devices. For example, the instrument deck may house one or more magnets 1710, which may be permanent magnets. Optionally, the instrument deck may house one or more electromagnets 1715. Magnets 1710 and/or electromagnets 1715 are positioned in relation to droplet actuator 1705 for immobilization of magnetically responsive beads. Optionally, the positions of magnets 1710 and/or electromagnets 1715 may be controlled by a motor 1720. Additionally, the instrument deck may house one or more heating devices 1725 for controlling the temperature within, for example, certain reaction and/or washing zones of droplet actuator 1705. In one example, heating devices 1725 may be heater bars that are positioned in relation to droplet actuator 1705 for providing thermal control thereof.

A controller 1730 of microfluidics system 1700 is electrically coupled to various hardware components of the apparatus set forth herein, such as droplet actuator 1705, electromagnets 1715, motor 1720, and heating devices 1725, as well as to a detector 1735, an impedance sensing system 1740, and any other input and/or output devices (not shown). Controller 1730 controls the overall operation of microfluidics system 1700. Controller 1730 may, for example, be a general purpose computer, special purpose computer, personal computer, or other programmable data processing apparatus. Controller 1730 serves to provide processing capabilities, such as storing, interpreting, and/or executing software instructions, as well as controlling the overall operation of the system. Controller 1730 may be configured and programmed to control data and/or power aspects of these devices. For example, in one aspect, with respect to droplet actuator 1705, controller 1730 controls droplet manipulation by activating/deactivating electrodes.

The controller 1730 is configured to execute program instructions to implement the processes described herein. The controller 1730 directs the droplet actuator to transport a sample droplet to a microwell device. The sample droplet includes cells of interest that enter the microwells. The controller 1730 further manages the system to introduce capture beads to the microwells, wherein capture elements are immobilized on the capture beads and directs the droplet actuator to transport a cell lysis reagent droplet to the microwell device. Portions of the lysis reagent droplet enter the microwells and, during an incubation period, cause the cells of interest to release analyte that is captured by the capture elements on the capture beads. The controller 1730 directs the droplet actuator to transport the sample droplet away from the microwell device while leaving at least a portion of the cells of interest captured in the microwells. The controller 1730 directs components of the system to remove the capture beads with the analyte captured thereon from the microwells. For example, the controller 1730 directs the magnets 1710 and/or electromagnets 1715 (positioned proximate to the microwells) to form a magnetic field that pulls the capture beads from the microwells. Optionally, the controller 1730 manages the magnets 1710 and electromagnets 1715 to utilize a magnetic field to move the capture beads to and away from the microwells.

In some embodiments, the system controller is further configured to execute program instructions to, during and/or prior to the incubation period, direct the droplet actuator to transport a fluid immiscible with the cell lysis reagent droplet to the microwell device, wherein the immiscible fluid does not enter the microwells and cell traps, thereby encapsulating single beads with single cells with cell lysis reagent.

In one example, detector 1735 may be an imaging system that is positioned in relation to droplet actuator 1705. In one example, the imaging system may include one or more light-emitting diodes (LEDs) (i.e., an illumination source) and a digital image capture device, such as a charge-coupled device (CCD) camera. Detection can be carried out using an apparatus suited to a particular reagent or label in use. For example, an optical detector such as a fluorescence detector, absorbance detector, luminescence detector or the like can be used to detect appropriate optical labels. Systems designed for array-based detection are particularly useful. For example, optical systems for use with the methods set forth herein may be constructed to include various components and assemblies as described in Banerjee et al., U.S. Pat. No. 8,241,573, entitled "Systems and Devices for Sequence by Synthesis Analysis," issued on Aug. 14, 2012; Feng et al., U.S. Pat. No. 7,329,860, entitled "Confocal Imaging Methods and Apparatus," issued on Feb. 12, 2008; Feng et al., U.S. Pat. No. 8,039,817, entitled "Compensator for Multiple Surface Imaging," issued on Oct. 18, 2011; Feng et al., U.S. Patent Pub. No. 20090272914, entitled "Compensator for Multiple Surface Imaging," published on Nov. 5, 2009; and Reed et al., U.S. Patent Pub. No. 20120270305, entitled "Systems, Methods, and Apparatuses to Image a Sample for Biological or Chemical Analysis," published on Oct. 25, 2012, the entire disclosures of which are incorporated herein by reference. Such detection systems are particularly useful for nucleic acid sequencing embodiments.

Impedance sensing system 1740 may be any circuitry for detecting impedance at a specific electrode of droplet actuator 1705. In one example, impedance sensing system 1740 may be an impedance spectrometer. Impedance sensing system 1740 may be used to monitor the capacitive loading of any electrode, such as any droplet operations electrode, with or without a droplet thereon. For examples of suitable capacitance detection techniques, see Sturmer et al., International Patent Pub. No. WO/2008/101194, entitled "Capacitance Detection in a Droplet Actuator," published on Dec. 30, 2009; and Kale et al., International Patent Pub. No. WO/2002/080822, entitled "System and Method for Dispensing Liquids," published on Feb. 26, 2004, the entire disclosures of which are incorporated herein by reference.

Droplet actuator 1705 may include disruption device 1745. Disruption device 1745 may include any device that promotes disruption (lysis) of materials, such as tissues, cells and spores in a droplet actuator. Disruption device 1745 may, for example, be a sonication mechanism, a heating mechanism, a mechanical shearing mechanism, a bead beating mechanism, physical features incorporated into the droplet actuator 1705, an electric field generating mechanism, a thermal cycling mechanism, and any combinations thereof. Disruption device 1745 may be controlled by controller 1730.

In some embodiments, the disclosure contemplates a digital fluidics system for capturing cells of interest, the system comprising: (a) a droplet actuator including a droplet operations gap, the droplet actuator including droplet operations electrodes arranged proximate to the droplet operations gap; (b) a microwell device including: (1) a first substrate, the microwell device including microwells formed in the first substrate, the microwells opening onto a droplet operations surface of the microwell device, the microwell device coupled to the droplet actuator and positioned such that the microwells face the droplet operations gap; and (2) a second substrate, the microwell device including cell traps formed on the second substrate, the cell traps opening onto the droplet operations surface of the microwell device; (c) a controller configured to execute program instructions to: (1) direct the droplet actuator to transport a sample droplet to a microwell device, the sample droplet including cells of interest that enter the cell traps; (2) introduce capture beads to the microwells, wherein capture elements are immobilized on the capture beads; and (3) direct the droplet actuator to transport a cell lysis reagent droplet to the microwell device, wherein portions of the lysis reagent droplet enter the cell traps and microwells and, during an incubation period, cause the cells of interest to release analyte that is captured by the capture elements on the capture beads.

In some embodiments of the system, the first substrate includes a hydrophobic layer disposed thereon, the hydrophobic layer forming the droplet operations surface. In some embodiments, the microwells have a size and pitch dimensioned to receive only a single one of the capture beads.

It will be appreciated that various aspects of the present disclosure may be embodied as a method, system, computer readable medium, and/or computer program product. Aspects of the present disclosure may take the form of hardware embodiments, software embodiments (including firmware, resident software, micro-code, etc.), or embodiments combining software and hardware aspects that may all generally be referred to herein as a "circuit," "module," or "system." Furthermore, the methods of the present disclosure may take the form of a computer program product on a computer-usable storage medium having computer-usable program code embodied in the medium.

Any suitable computer useable medium may be utilized for software aspects of the present disclosure. The computer-usable or computer-readable medium may be, for example but not limited to, an electronic, magnetic, optical, electromagnetic, infrared, or semiconductor system, apparatus, device, or propagation medium. The computer readable medium may include transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the methods and apparatus set forth herein may be written in an object oriented programming language such as Java, Smalltalk, C++ or the like. However, the program code for carrying out operations of the methods and apparatus set forth herein may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The methods and apparatus set forth herein may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The methods and apparatus set forth herein may be applied to any wireless/wireline communications network, regardless of physical componentry, physical configuration, or communications standard(s).

Certain aspects of present disclosure are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the present disclosure.

CONCLUSION

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

The invention claimed is:

1. A method comprising:
   (a) utilizing a droplet actuator to transport a sample droplet to a microwell device, the sample droplet including cells of interest, the microwell device including
      a bottom substrate having a plurality of microwells that open onto a droplet operations surface of the microwell device, and
      a top substrate comprising a plurality of molded cell traps that extend into the droplet operations surface of the microwell device and are located above each of the plurality of microwells, wherein the plurality of microwells and the plurality of molded cell traps are configured such that the cells of interest are trapped by the plurality of molded cell traps and are thereby deposited into the plurality of microwells;
   (b) introducing capture beads to the microwells, wherein capture elements are immobilized on the capture beads; and
   (c) utilizing the droplet actuator to transport a cell lysis reagent droplet to the microwell device, wherein portions of the cell lysis reagent droplet enter the microwells and, during an incubation period, cause the cells of interest to lyse and release analyte that is captured by the capture elements on the capture beads.

2. The method of claim 1, wherein the capture beads are sized such that only one of the capture beads fits in one of the microwells.

3. The method of claim 1, wherein the molded cell traps are sized such that only one of the cells of interest fits in one of the molded cell traps.

4. The method of claim 1, further comprising:
   (d) during and/or prior to the incubation period, utilizing the droplet actuator to transport a fluid immiscible with the cell lysis reagent droplet to the microwell device, wherein the immiscible fluid does not enter the microwells and molded cell traps, thereby encapsulating single beads with single cells with cell lysis reagent.

5. The method of claim 1, further comprising removing the capture beads with the analyte captured thereon from the microwells.

6. The method of claim 5, wherein the removing operation includes positioning a magnet proximate to the microwells to form a magnetic field that pulls the capture beads from the microwells.

7. The method of claim 1, further comprising utilizing a magnetic field to move the capture beads to and away from the microwells.

8. The method of claim 1, wherein each of the capture beads includes a plurality of the capture elements.

9. The method of claim 8, wherein the plurality of capture elements include a capture sequence and a unique barcode sequence, wherein the capture sequence is optionally one of i) a poly-T sequence for capture of total mRNA, or ii) a plurality of transcript-specific capture sequences that target a panel of genes of interest.

* * * * *